United States Patent [19]

Takeda

[11] Patent Number: 4,533,678

[45] Date of Patent: Aug. 6, 1985

[54] BASIC COMPOUND, ITS POLYMER, A PROCESS FOR THE PREPARATION THEREOF AND ITS USE AS ION EXCHANGE RESIN

[75] Inventor: Kunihiko Takeda, Yokohama, Japan

[73] Assignee: Asahi Kasei Kogyo Kabushiki Kaisha, Osaka, Japan

[21] Appl. No.: 589,210

[22] Filed: Mar. 13, 1984

[30] Foreign Application Priority Data

| Mar. 23, 1983 | [JP] | Japan | 58-47112 |
| Mar. 23, 1983 | [JP] | Japan | 58-47113 |
| Mar. 23, 1983 | [JP] | Japan | 58-48477 |
| Mar. 23, 1983 | [JP] | Japan | 58-48478 |
| Mar. 29, 1983 | [JP] | Japan | 58-53316 |

[51] Int. Cl.$^3$ ............ C07D 235/04; C07D 487/00; C08F 8/32; B01J 39/20
[52] U.S. Cl. .................. 521/389; 548/333; 548/334; 526/261; 526/262; 526/259; 525/326.7
[58] Field of Search .......... 526/259, 262, 261; 548/333, 334; 525/326.7; 521/38

[56] References Cited

U.S. PATENT DOCUMENTS

| 2,643,990 | 6/1953 | Ham | 548/333 |
| 2,965,647 | 12/1960 | Wilgand et al. | 548/334 |
| 3,247,217 | 4/1966 | Grewe et al. | 548/305 |
| 3,912,697 | 10/1975 | Pacifici | 526/259 |
| 4,192,880 | 3/1980 | Tsukamoto et al. | 548/334 |
| 4,412,011 | 10/1983 | Kihara et al. | 521/38 |
| 4,430,445 | 2/1984 | Miyake et al. | 521/38 |

FOREIGN PATENT DOCUMENTS 853374  11/1960  United Kingdom ............ 548/334

OTHER PUBLICATIONS

Collection Czechoslov. Chem. Commun., vol. 31, pp. 4682–4693, (1966).
Journal of Heterocyclic Chemistry, vol. 2,(4), pp. 453–456, (1965).
Tetrahedron Letters No. 38, pp. 3541–3544, (1971).
Benzimidazoles and Congeneric Tricyclic Compounds, Part I, pp. 14–17.
Chem. Abstracts, vol. 74, entry 53645, (1971), Furst et al.
Chem. Abstracts, vol. 95, entry 203830e, Topukh, et al.

*Primary Examiner*—Joseph L. Schofer
*Assistant Examiner*—Peter F. Kulkosky
*Attorney, Agent, or Firm*—Sprung Horn Kramer & Woods

[57] ABSTRACT

Novel benzimidazolyl compounds which are basic compounds and have high polymerizability are disclosed. The basic compound of the present invention is prepared by reacting a vinylbenzaldehyde with an o-phenylenediamine compound, and can be used, for example, as a monomer for polymers. The benzimidazolylstyrene compounds are readily homopolymerized or copolymerized to provide linear homopolymers, linear copolymers or cross-linked copolymers having pendant benzimidazolylphenyl groups. These polymers have greater resistance to oxidation and chemicals than the homologues, and are useful as ion exchange resins, and as extractants of metals.

37 Claims, No Drawings

BASIC COMPOUND, ITS POLYMER, A PROCESS FOR THE PREPARATION THEREOF AND ITS USE AS ION EXCHANGE RESIN

This invention relates to a novel basic compound, its polymer, a process for the preparation thereof and its use as an ion exchange resin. More particularly, this invention is concerned with a basic compound having a benzimidazole ring or a benzimidazolium ring and capable of being homopolymerized and copolymerized, a process for the preparation thereof, a linear homopolymer, linear copolymer and cross-linked copolymer having pendant benzimidazolylphenyl or benzimidazoliumphenyl groups, a process for the preparation thereof and the use of the cross-linked copolymer as an ion exchange resin.

Many monomers having a basic group are known and used as materials for functional polymers or drugs. As an example of a compound having a benzimidazole ring, 2-(o-iso-propenylphenyl)benzimidazole, 2[o-(1-ethyl-propenyl)phenyl]-benzimidazole, etc., are disclosed in Collect. Czech. Chem. Commun, 31(12) 4682(1966). These compounds, however, are difficult to polymerize, so that a polymer having a high molecular weight is not yet obtained from them.

Also known are monomers having a vinyl group and a basic group, such as vinylimidazole, vinylpyridine and vinylcarbazole. However the polymers of these monomers are chemically and thermally unstable and consequently they are used only under limited conditions or have short lives.

We have studied the synthesis of a monomer having benzimidazole ring and its ability to polymerize similarly to styrene and, as a result, we have succeeded in synthesizing novel basic monomers, more particularly benzimidazolylstyrene compounds or benzimidazoliumstyrene compounds, which are basic due to the inherent nature of the benzimidazole ring and can be radical polymerized. We have further studied the polymerizability of the benzimidazolylstyrene compounds or benzimidazoliumstyrene compounds, and have found that they can be copolymerized at an optional molar ratio with a typical monomer such as styrene, methyl methacrylate or divinylbenzene. We have attempted various homopolymerization and copolymerization reactions, whereby we have obtained various useful homopolymers and copolymers. Based on these findings, we have completed this invention.

It is, therefore, an object of the present invention to provide a novel class of benzimidazolylstyrene or benzimidazoliumstyrene compounds which have high polymerizability.

It is another object of the present invention to provide a process for the preparation of such a novel class of benzimidazolystyrene or benzimidazoliumstyrene compounds.

It is a further object of the present invention to provide a linear homopolymer, linear copolymer and cross-linked copolymer having pendant benzimidazolylphenyl or benzimidazoliumphenyl groups which can be advantageously used as an ion exchange resin, a metal extractant or for other purposes.

It is still a further object of the present invention to provide a process for the preparation of such a linear homopolymer, linear copolymer and cross-linked copolymer.

It is an additional object of the present invention to provide a method of ion exchange using a cross-linked copolymer having pendant benzimidazolylphenyl or benzimidazoliumphenyl groups as an ion exchange resin.

The foregoing and other objects, features and advantages of the present invention will be apparent to those skilled in the art from the following detailed description and appended claims.

In accordance with one aspect of the present invention, there is provided a basic compound of Formula (1):

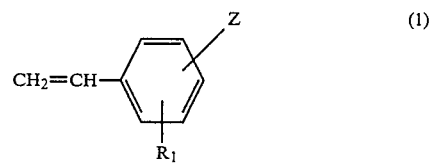

wherein $R_1$ is a hydrogen atom or a straight chain or branched hydrocarbon group having 1 to 4 carbon atoms, Z is a group of Formula (2) or Formula (3).

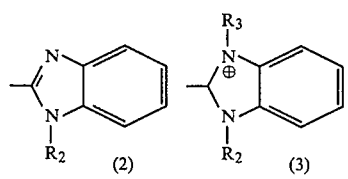

wherein $R_2$ and $R_3$ each independently is a hydrogen atom, a straight chain or branched hydrocarbon group having 1 to 10 carbon atoms or a carboxyalkyl group having 2 to 10 carbon atoms.

As preferred examples of $R_1$, there can be mentioned a hydrogen atom, a methyl group and an ethyl group, the hydrogen atom being more preferable.

As preferred examples of $R_2$ and $R_3$, there can be mentioned a hydrogen atom, a methyl group, an ethyl group, a normal propyl group, an isopropyl group, a butyl group, a benzyl group and a carboxymethyl group, the hydrogen atom, methyl group, ethyl group, benzyl group and carboxymethyl group being more preferable. $R_2$ and $R_3$ may be the same or different.

The position of $R_1$ or Z relative to the vinyl group in the compound of Formula (1) may be the ortho-, meta- or para-position, and is preferably the meta- or para-position.

The benzimidazolium ion represented by Formula (3) should have a counter ion (X). X may be a monovalent or polyvalent anion. When it is a polyvalent anion, it may pair with plural benzimidazolium cations to form a salt.

As preferred examples of X, there can be mentioned a halogen ion, a hydroxy ion, a carbonate ion, a sulfate ion, a nitrate ion, a phosphate ion, etc.

In accordance with a second aspect of the present invention, there is provided a process for the preparation of a basic compound of Formula (1):

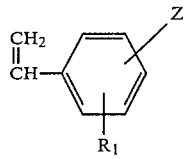

wherein $R_1$ and Z are as defined above.

Of these basic compounds, the compound whose Z is a group of Formula (2), is prepared by reacting a vinylbenzaldehyde of Formula (8):

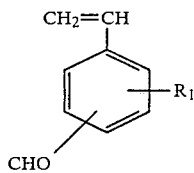

wherein $R_1$ is as defined above, with an o-phenylenediamine of Formula (9):

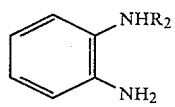

wherein $R_2$ is as defined above.

The position of $R_1$ of the aldehyde group relative to the vinyl group in the compound of Formula (8) is not critical.

As the vinylbenzaldehyde of the Formula (8) that can be preferably used in the process of the present invention, there can be mentioned, for example, para- and meta-vinylbenzaldehyde, 1-methyl-3-vinyl-5-formylbenzene and 1-ethyl-3-vinyl-5-formylbenzene.

As the o-phenylenediamine of Formula (9) that can be preferably used in the process of the present invention, there can be mentioned, for example, o-phenylenediamine, N-methyl-o-phenylenediamine, N-ethyl-o-phenylenediamine, N-propyl-o-phenylenediamine and N-benzyl-o-phenylenediamine.

The o-phenylenediamine may also be used in the form of a salt such as a hydrochloric acid salt.

The charging molar ratio of the o-phenylenediamine compound of Formula (9) to the vinylbenzaldehyde compound of Formula (8) is not critical, but preferably is in the range of 0.1 to 10.

The reaction temperature is not critical, but usually in the range of from 0° C. to 150° C., preferably from 20° C. to 100° C.

The reaction time is not critical, but the reaction may usually be carried out for 30 minutes to 10 hours. Since the reaction rate varies depending on the reaction temperature, the amount of inert solvent if used, the amount and kind of reaction promoter if used, and the like, it is preferred that the progress of the reaction be monitored by periodically determining the amount of the desired product formed by means of liquid chromatography or the like.

The reaction of the present invention may be carried out either in the presence or absence of an inert solvent. As the inert solvent, there can be mentioned, for example, water; aliphatic hydrocarbons such as pentane, hexane, heptane and octane; alcohols such as methanol, ethanol and isopropyl alcohol; ketones such as acetone, methyl ethyl ketone and diethyl ketone; ethers such as diethyl ether, methyl ethyl ether, dibutyl ether, diphenyl ether, dioxane and tetrahydrofuran; aromatic hydrocarbons such as benzene, toluene and xylene; esters such as ethyl formate, ethyl acetate and butyl acetate; amides such as dimethyl formamide and dimethyl acetamide; halogenated aliphatic hydrocarbons such as chloroform, methylene chloride and dichloroethane; halogenated aromatic hydrocarbons such as chlorobenzene; and sulfoxides such as dimethyl sulfoxide. They may be used either alone or in mixtures. If an inert solvent is used in the reaction, the amount of the inert solvent cannot be determined independently because the solubility of the vinylbenzaldehyde and/or the o-phenylenediamine compound in the solvent must be taken into consideration. It is preferred that the inert solvent is used at least in a minimum amount necessary for providing a homogeneous reaction system. The inert solvent is usually used in an amount of 0 to 1,000 liters, preferably 0 to 100 liters, per mole of the vinylbenzaldehyde.

We have found that if the reaction of the present invention is carried out in the presence of a polymerization inhibitor, a high reaction temperature and/or high concentrations of the reactants can be employed so that the rate of reaction can be accelerated. As the polymerization inhibitor, there can be mentioned, for example, derivatives of phenol such as tert-butylcatechol, 2-tert-butyl-4-hydroxyanisole, 2,6-di-tert-butyl-4-methylphenol, 4,4'-thiobis(6-tert-butyl-3-methylphenol) and 4,4'-butylidenebis-(6-tert-butyl-3-methylphenol); derivatives of hydroquinones such as tert-butylhydroquinone and 2,5-di-tert-butylhydroquinone; nitroso group- and/or hydroxylamino group-containing compounds such as n-butyl nitrite and the ammonium salt of N-nitrosophenylhydroxylamine (cupferron); and organic halide compounds such as dibromobenzene and trichlorobenzene. They may be used either alone or in mixture.

The addition of a polymerization inhibitor to the reaction system is not necessarily needed, but it is preferred that it be present because it inhibits or minimizes the advance of polymerization of the vinylbenzaldehyde and/or the product and, hence, permits a higher reaction temperature so that the reaction time may be shorter.

The inhibitor is usually used in an amount of 5 wt. % or less based on the weight of vinylbenzaldehyde.

It is preferred that a reaction promotor is added to the reaction system. The reaction promotor is a material which is able to increase the reaction rate by reacting with the vinylbenzaldehyde or o-phenylenediamine.

As the reaction promotor of the present invention, there can be used a compound of the formula $(Met)_k H_l S_m O_n$ wherein Met is an alkali metal or an alkaline earth metal having a valence, of "a", k, l, m and n are zero or positive integers, and $ak + l + 4m = 2n$ or $ak + l + 6m = 2n.$ As the reaction promotor, there can be mentioned, for example, sulfur dioxide; sulfurous acid salts of alkali metals or alkaline earth metals such as sodium sulfite, sodium hydrogensulfite and calcium sulfite; thiosulfuric acid salts of alkali metals or alkaline earth metals such as sodium thiosulfate and calcium thiosulfate; and metahydrogen sulfinic acid salts such as sodium metabisulfite.

The molar ratio of the reaction promotor to the amount of a vinylbenzaldehyde is usually 0.1 or more, preferably in 0.1 to 10, and more preferably in 0.5 to 3.

The reaction promotor may be first reacted previously with the vinylbenzaldehyde or o-phenylenediamine or it may be added to the mixture of vinylbenzaldehyde and o-phenylenediamine.

The compound of Formula (1) wherein Z is a group of Formula (3) may be prepared by reacting a compound of Formula (1) wherein Z is a group of Formula (2) with a compound $R_3Y$ ($R_3$ is the same as defined above and Y is a halogen atom).

The compound of Formula (1) wherein Z is a group of Formula (3) and at least one of $R_2$ and $R_3$ is a hydrogen atom, is an ammonium cation and can be prepared by the reaction of an acid with the corresponding compound of Formula (1) having a group of Formula (2) instead of a group of Formula (3). The molar ratio of the acid to the group of Formula (2) in the compound of Formula (1) is usually one or more.

In this case, the conversion between a group of Formula (3) and a group of Formula (2) occurs reversibly by adding an acid or a base.

The compound of Formula (1) wherein Z is a group of Formula (3) and neither $R_2$ nor $R_3$ is a hydrogen atom, can be prepared by the reaction of the corresponding compound having a group of Formula (2) instead of a group of Formula (3) with a compound represented by the formula $R_3Y$ ($R_3$ is as defined above and Y is a halogen atom). The molar ratio of the compound of $R_3Y$ to the group of Formula (2) in the compound of Formula (1) is preferably one or more, more preferably 1 to 10.

The compound of Formula (1) wherein Z is a group of Formula (3) and $R_2$ and $R_3$ are the same and not hydrogen atoms, can be further prepared by the reaction of a compound of Formula (1) wherein Z is a group of Formula (2) and $R_2$ is a hydrogen atom, with a compound represented by the formula of $R_3Y$ (=$R_2Y$, $R_3$ is as defined above but not a hydrogen atom and Y is a halogen atom).

In this reaction, 2 moles of the compound of $R_3Y$ react with one mole of the group of Formula (2) in the compound of Formula (1), theoretically.

In this case, a compound of Formula (1) wherein Z is a group of Formula (3) and at least one of $R_2$ and $R_3$ is a hydrogen atom, may be byproduced.

The conditions of the reaction of a compound of Formula (1) wherein Z is a group of Formula (2) and a compound $R_3Y$ described above, are usually as follows.

The reaction temperature is not critical, but usually in the range of 20° C. to 150° C.

The reaction time is not critical, but the reaction may usually be carried out for 1 to 50 hours.

The reaction may be carried out in the presence of an inert solvent.

As the inert solvent, there can be mentioned, for example, water; aliphatic hydrocarbons such as pentane, hexane, heptane and octane; alcohols such as methanol, ethanol and isopropyl alcohol; ketones such as acetone, methyl ethyl ketone and diethyl ketone; ethers such as diethyl ether, methyl ethyl ether, dibutyl ether, diphenyl ether, dioxane and tetrahydrofuran; aromatic hydrocarbons such as benzene, toluene and xylene; esters such as ethyl formate, ethyl acetate and butyl acetate; amides such as dimethyl formamide and dimethyl acetamide; halogenated aliphatic hydrocarbons such as chloroform, methylene chloride and dichloroethane; halogenated aromatic hydrocarbons such as chlorobenzene; and sulfoxides such as dimethyl sulfoxide. They may be used either alone or in mixtures. The inert solvent is usually used in an amount of 0 to 1,000 liters, preferably 0 to 100 liters, per mole of the compound of Formula (1).

In this reaction, a basic compound may be added to the reaction system. As the basic compound, there can be mentioned, for example, a salt of an alkali metal or an alkaline earth metal such as sodium hydroxide, potassium hydroxide and sodium carbonate and an alcoholate of an alkali metal or an alkaline earth metal such as sodium ethylate. The charging molar ratio of basic compound to compound of Formula (1) is not critical, but preferably is 0.1 to 10, more preferably 1 to 3.

In the case of preparing the compound of Formula (1) wherein Z is a group of Formula (3), using the compound of Formula (1) wherein Z is a group of Formula (2) and $R_2$ is a hydrogen atom, the addition of the basic compound shows good results.

The basic compound of Formula (1) wherein Z is a group of Formula (2) and $R_2$ is a hydrocarbon group or a carboxyalkyl group may also be prepared by reacting a halogenated hydrocarbon or a carboxymethylhalide with the compound of Formula (1) wherein Z is a group of Formula (2) and $R_2$ is a hydrogen atom.

In this case, the compound of Formula (1) wherein Z is a group of Formula (3) might be byproduced.

The basic compound of Formula (1) according to the present invention can advantageously be used, for example, as a monomer for homopolymerization or copolymerization with other monomers to give various polymers.

In accordance with a third aspect of the present invention, there is provided a linear homopolymer comprising recurring units of Formula (4):

$$-CH_2-CH- \quad (4)$$

(structure: $-CH_2-CH-$ attached to a benzene ring bearing $R_1$ and $Z$)

wherein $R_1$ is a hydrogen atom or a straight chain or branched hydrocarbon group having 1 to 4 carbon atoms, Z is a group of Formula (2) or Formula (3):

(Formula (2): benzimidazole group with $R_2$ on one N;
Formula (3): benzimidazolium cation with $R_2$ and $R_3$ on the two N atoms)

wherein $R_2$ and $R_3$ each independently is a hydrogen atom, a straight chain or branched hydrocarbon group having 1 to 10 carbon atoms or a carboxyalkyl group having 2 to 10 carbon atoms, having a number-average molecular weight of about 1,000 to about 2,000,000.

As preferred examples of $R_1$, there can be mentioned a hydrogen atom, a methyl group and an ethyl group, the hydrogen atom being more preferable.

As preferred examples of $R_2$ and $R_3$, there can be mentioned a hydrogen atom, a methyl group, an ethyl group, a normal propyl group, an isopropyl group, a butyl group, a benzyl group and a carboxymethyl group, the hydrogen group, methyl group, ethyl group, benzyl group and carboxymethyl group being more preferable. $R_2$ and $R_3$ may be the same or different.

The position of $R_1$ or Z relative to the main chain of units of the Formula (4) may be the ortho-, meta- or para-position, and is preferably the meta- or para-position.

The benzimidazolium ion represented by Formula (3) should have a counter ion (X).

X may be a monovalent or polyvalent anion. When it is a polyvalent anion, it may pair with plural benzimidazolium cations to form a salt.

As preferred examples of X, there can be mentioned a halogen ion, a hydroxy ion, a carbonate ion, a sulfate ion, a nitrate ion, a phosphate ion, etc.

The linear homopolymer of the present invention may have different units of Formula (4), differing in $R_1$ and/or Z.

The linear homopolymer of the present invention is useful as an extractant of metals such as Fe, Cu, Mn, Sn, U, Pt, Hg, Au, Ce and Pr.

In accordance with a fourth aspect of the present invention, there is provided a process for the preparation of a linear homopolymer of Formula (4) which comprises polymerizing a basic monomer of Formula (1).

For preparing a linear homopolymer of Formula (4), any of the customary polymerization procedures can be employed. The compound of Formula (1) can be heat polymerized, but it may be preferred that a polymerization initiator be added.

As the polymerization initiator employed according to the present invention, there can be mentioned, for example, acyl peroxides such as benzoyl peroxide and lauroyl peroxide; azonitriles such as azobisisobutyronitrile and 2,2′-azobis-(2,4-dimethylvaleronitrile); peroxides such as ditert-butyl peroxide, dicumyl peroxide and methyl ethyl ketone peroxide; and hydroperoxides such as cumenyl hydroperoxide and tertiary hydroperoxide.

The amount of the polymerization initiator which can be employed in this invention is generally 0.01 to 5% by weight based on the weight of the basic compound of Formula (1). A preferred amount is 0.1 to 2% by weight.

The linear homopolymer according to the present invention may be produced by conducting polymerization either in the presence or absence of an inert solvent. Exemplary inert solvents which can be employed include aliphatic hydrocarbons such as n-pentane, n-hexane, n-heptane and n-octane; alcohols such as methanol, ethanol and isopropyl alcohol; ketones such as acetone, methyl ethyl ketone and diethyl ketone; ethers such as diethyl ether, methyl ethyl ether, dibutyl ether, dioxane and tetrahydrofuran; aromatic hydrocarbons such as benzene, toluene and xylenes; esters such as ethyl formate, ethyl acetate and butyl acetate; amides such as dimethyl formamide and dimethyl acetamide; halogenated aliphatic hydrocarbons such as chloroform, methylene chloride and dichloroethane; halogenated aromatic hydrocarbons such as chlorobenzene; and sulfoxides such as dimethyl sulfoxide. These solvents may be used either alone or in mixtures.

The amount of these inert solvents is usually not more than about 1000% by weight based on the total weight of monomer.

The reaction temperature is not critical but the reaction may usually be carried out at a temperature of 20° C. to 120° C., preferably 60° C. to 100° C.

The polymerization period is not critical, but the polymerization may usually be carried out for 1 to 50 hours.

In accordance with a fifth aspect of the present invention, there is provided a linear copolymer comprising about 98 to about 10 mol % of recurring units of Formula (4),

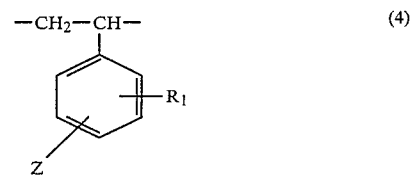

wherein $R_1$ and Z are the same as defined above, and about 2 to about 90 mol % of recurring units of Formula (7),

wherein P and Q each independently is a hydrogen atom, a halogen atom, a cyano group, an aryl group, a halogenophenyl group, a phenyl group substituted with one or more substituents selected from $C_1$–$C_5$ straight chain or branched alkyl and haloalkyl groups, —COOR$_9$ in which R$_9$ is a hydrogen atom or R$_{10}$, R$_{10}$ is a $C_1$–$C_{10}$ hydrocarbon residue, —COR$_9$, —OCOR$_{10}$, —CONHR$_9$, an imidazolyl group, a pyridyl group or a carbazolyl group, based on the total moles of the recurring units of Formula (4) and Formula (7), and having a number-average molecular weight of about 1,000 to about 2,000,000.

In accordance with a sixth aspect of the present invention, there is provided a cross-linked copolymer comprising about 98 to about 10 mol % of recurring units of Formula (4), about 2 to about 50 mol % of either or both of the recurring units of Formula (5) and Formula (6),

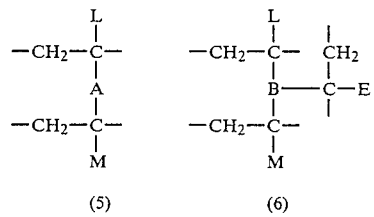

wherein L, M and E each independently is a hydrogen atom or a methyl group; A is

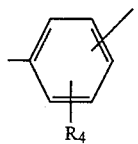

wherein $R_4$ is a hydrogen atom or a $C_1$-$C_5$ hydrocarbon residue;

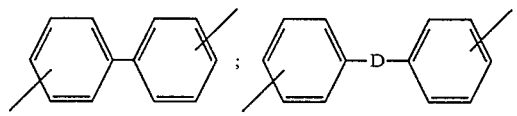

wherein D is —O—, —S—, —NH— or a divalent $C_1$-$C_5$ hydrocarbon residue;

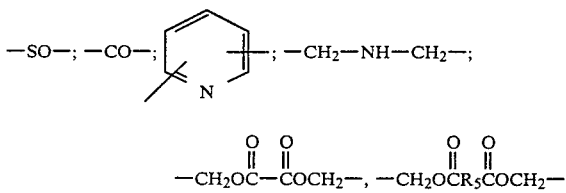

wherein $R_5$ is a divalent $C_1$-$C_8$ hydrocarbon residue;

wherein $R_6$ is a divalent $C_1$-$C_5$ hydrocarbon residue; or

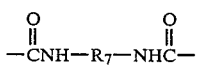

wherein $R_7$ is a divalent $C_1$-$C_3$ hydrocarbon residue; and B is

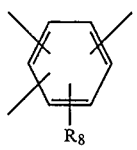

wherein $R_8$ is a hydrogen atom or a $C_1$-$C_5$ hydrocarbon residue;

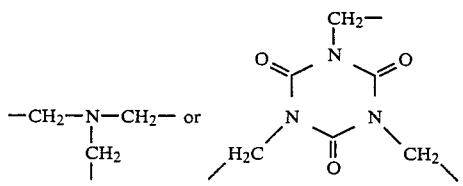

and 0 to about 88 mol % of the recurring units of Formula (7) based on the total moles of the recurring units of Formula (4), Formula (5), Formula (6) and Formula (7).

In the recurring units of Formula (4) in the above described linear copolymer and the above described cross-linked copolymer, the position of $R_1$ or Z relative to the vinyl group may be the ortho-, meta- or para-position, and is preferably the meta- or para-position.

As preferred examples of $R_1$ in the recurring units of Formula (4) in these copolymers, there can be mentioned a hydrogen atom, a methyl group and an ethyl group, the hydrogen atom being more preferable.

As preferred examples of $R_2$ and $R_3$ in the group of Formula (2) or (3), there can be mentioned a hydrogen atom, a methyl group, an ethyl group, a propyl group, a butyl group, a benzyl group and a carboxymethyl group, the hydrogen atom, methyl group, ethyl group, benzyl group and carboxymethyl group being more preferable.

It is not necessary that $R_1$ or Z in the recurring units of Formula (4) be the same, and the above described copolymers may have recurring units of Formula (4) with different $R_1$ and/or Z radicals.

Preferred examples of P and Q in the recurring units of Formula (7) include a hydrogen atom, a cyano group, a chlorine atom, a methyl group, a phenyl group, a COOH group, a $COOCH_3$ group, a $COCH_3$ group, an $OCOCH_3$ group, a $CONH_2$ group, a $COOC_6H_5$ group and a hydroxymethylphenyl group.

The copolymers of this invention may have the recurring units of Formula (7) with different P and/or Q radicals.

As preferred examples of A in the recurring units of Formula (5), there may be mentioned

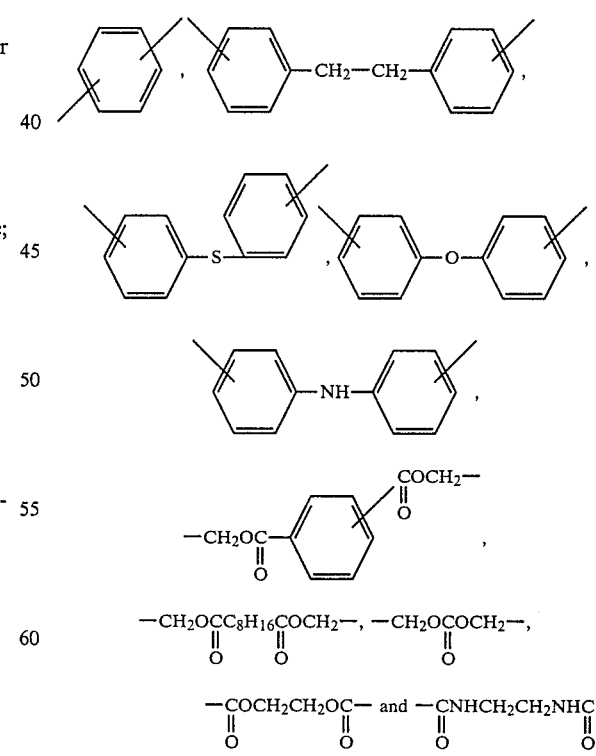

The cross-linked copolymer may have recurring units of Formula (5) or Formula (6) with different A, B, L, M and/or E radicals.

The linear copolymer of this invention has a number-average molecular weight of about 1,000 to about 2,000,000, preferably about 1,000 to about 1,000,000.

In the linear copolymer, the amount of recurring units of Formula (4) is about 10 to about 98 mol %, preferably about 20 to about 98 mol % based on the total moles of recurring units of Formula (4) and Formula (7).

In the cross-linked copolymer, the amount of recurring units of Formula (4) is about 10 to about 98 mol %, preferably about 20 to about 98 mol %, the amount of recurring units of Formula (5) and/or Formula (6) is about 2 to about 50 mol %, preferably about 2 to about 30 mol % and recurring units of Formula (7) is 0 to about 88 mol % based on the total moles of recurring units of Formula (4), Formula (5), Formula (6) and Formula (7).

The linear copolymer of this invention is useful as an extractant of metals and the cross-linked copolymer of this invention is useful as an ion exchange resin having an excellent resistance to oxidation and chemicals.

In accordance with a seventh aspect of the present invention, there is provided a process for the preparation of the linear copolymer comprising about 98 to about 10 mol % of recurring units of Formula (4) and about 2 to about 90 mol % of recurring units of Formula (7) based on the total moles of recurring units of Formula (4) and Formula (7) and having a number-average molecular wiehgt of about 1,000 to about 2,000,000, which comprises copolymerizing about 98 to about 10 mol % of the basic compound of Formula (1), and about 90 to about 2 mol % of a monomer of Formula (12),

(12)

wherein P and Q are the same as defined above, based on the total moles of basic compound of Formula (1) and monomer of Formula (12).

In accordance with an eighth aspect of the present invention, there is provided a process for the preparation of the cross-linked copolymer comprising about 98 to about 10 mol % of recurring units of Formula (4), about 2 to about 50 mol % of either or both of recurring units of Formula (5) and Formula (6), and 0 to about 88 mol % of recurring units of Formula (7) based on the total moles of recurring units of Formula (4), Formula (5), Formula (6) and Formula (7) which comprises copolymerizing about 98 to about 10 mol % of the basic compound of Formula (1), about 2 to about 50 mol % of at least one monomer of Formula (10) plus Formula (11);

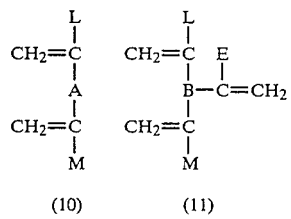

wherein L, M, E, A and B are the same as defined above, and 0 to about 88 mol % of monomer of Formula (12) based on the total moles of basic compound of Formula (1), monomer of Formula (10), the monomer of Formula (11) and monomer of Formula (12).

In copolymerizing the basic compound of Formula (1) with the monomer of Formula (12) or the basic compound of Formula (1) with at least one monomer of Formula (10) plus Formula (11), and if desired, the monomer of Formula (12), any of the conventional polymerization procedures can be employed. A mixture of the monomers can be heat polymerized, but it may be preferred that a polymerization initiator be added. Exemplary polymerization initiators employed according to the present invention include acyl peroxides such as benzoyl peroxide and lauroyl peroxide; azonitriles such as azobisisobutyronitrile and 2,2'-azobis(2,4-dimethylvaleronitrile); peroxides such as ditert-butyl peroxide, dicumyl peroxide and methyl ethyl ketone peroxide; and hydroperoxides such as cumenyl hydroperoxide and tertiary butyl hydroperoxide. The amount of the polymerization initiator which can be employed in this invention is generally 0.01 to 5% by weight, preferably 0.1 to 2% by weight on the total weight of the monomers employed.

The copolymers according to the present invention may be produced by copolymerization either in the presence or absence of an inert solvent. As the inert solvent, there can be mentioned, for example, aliphatic hydrocarbons such as n-pentane, n-hexane, n-heptane and n-octane; alcohols such as methanol, ethanol and isopropyl alcohol; ketones such as acetone, methyl ethyl ketone and diethyl ketone; ethers such as diethyl ether, methyl ethyl ether, dibutyl ether, dioxane and tetrahydrofuran; aromatic hydrocarbons such as benzene, toluene and xylenes; esters such as ethyl formate, ethyl acetate and butyl acetate; amides such as dimethyl formamide and dimethyl acetamide; halogenated aliphatic hydrocarbons such as chloroform, methylene chloride and dichloroethane; halogenated aromatic hydrocarbons such as chlorobenzene; and sulfoxides such as dimethyl sulfoxide. These solvents may be used either alone or in mixtures.

The amount of inert solvent is preferably in the range of 0 to 1,000 volume % based on monomer or monomer mixture.

The reaction temperature is not critical but the reaction may usually be carried out at a temperature of 20° C. to 120° C., preferably 60° C. to 100° C.

The copolymerization time is not critical but the copolymerization may usually be carried out for about 1 to 50 hours.

Exemplary basic compounds of Formula (1) of the present invention include 2-(m-vinylphenyl)benzimidazole, 2-(p-vinylphenyl)benzimidazole, 2-(3-methyl-5-vinylphenyl)benzimidazole, 2-(3-ethyl-5-vinylphenyl)benzimidazole, 2-(3-benzyl-5-vinylphenyl)benzimidazole, 1-methyl-2-(vinylphenyl)benzimidazoliumchloride, 1,3-dimethyl-2-(vinylphenyl)benzimidazoliumchloride, 1-methyl-2-(3-methyl-5-vinylphenyl)benzimidazoliumchloride, 1-methyl-2-(3-ethyl-5-vinylphenyl)benzimidazoliumchloride, 1-methyl-2-(3-benzyl-5-vinylphenyl)benzimidazoliumchloride, 1,3-dimethyl-2-(methyl-5-vinylphenyl)benzimidazoliumchloride, 1,3-dimethyl-2-(3-ethyl-5-vinylphenyl)benzimidazoliumchloride, 1-methyl-3-ethyl-2-(vinylphenyl)benzimidazoliumbromide and 1-methyl-3-benzyl-2-(vinylphenyl)benzimidazoliumchloride. These compounds may be used in the process for the preparation of the linear homopolymer, the linear copolymer or the cross-linked copolymer of the present either alone or in mixtures.

Exemplary monomers of Formula (12) which can be employed in the process according the present invention include styrenes such as styrene, methylstyrene, ethylstyrene, diphenylethylene, dimethylstyrene, vinylbenzoic acid, vinylbenzyl alcohol, vinylphenol, ethyl vinyl benzoic acid, ethyl vinyl benzyl alcohol, vinyl mesitylene, 3,4,6-trimethyl styrene, chlorostyrene, methoxystyrene, bromostyrene, cyanostyrene, fluorostyrene, dichlorostyrene, N,N-dimethylaminostyrene, nitrostyrene, chloromethylstyrene, trifluorostyrene, trifluoromethylstyrene and aminostyrene; polycyclic aryl compounds such as vinylnaphthalene, vinylanthracene and vinylphenanthrene; unsaturated aliphatic hydrocarbons such as 1-vinyl-2-ethyl-acetylene, butadiene, isoprene and 1,3-pentadiene; vinylsulfides such as methylvinyl sulfide and phenyl vinylsulfide, acrylonitriles such as acrylonitrile, methacrylonitrile and α-acetoxyacrylonitrile; acrylic acid, methacrylic acid; acrylates such as methyl acrylate, lauryl acrylate, chloromethyl acrylate and ethyl acetoxyacrylate; methacrylates such as cyclohexyl methacrylate, dimethylaminoethyl methacrylate, glycidyl methacrylate, tetrahydrofurfryl methacrylate and hydroxyethyl methacrylate; diethyl maleate, diethyl fumarate; vinyl ketones such as methyl vinyl ketone and ethyl isopropenyl ketone; vinylidene compounds such as vinylidene chloride, vinylidene bromide and vinylidene cyanide; acrylamides such as acrylamide, methacrylamide, N-phenylacrylamide, diacetoneacrylamide, N-butoxymethylacrylamide and N,N-dimethylaminoethylacrylamide; esters of vinyl alcohol and aliphatic acid such as vinyl acetate, vinyl butyrate and vinyl caproate; thioesters such as phenylthiomethacrylate, methyl thioacrylate and vinyl thioacetate; heterocyclic vinyl compounds such as N-vinylsuccinimide, N-vinylpyrrolidone, N-vinylphthalimide, N-vinylcarbazole, vinylfurane, 2-vinylbenzofurane, vinylthiophene, vinylimidazole, methylvinylimidazole, vinylpyrazole, vinyloxazolidone, vinyltriazole, vinyltetrazole, vinylpyridine, methylvinylpyridine, 2,4-dimethyl-6-vinyltriazine and vinylquinoline. These compounds may be used either alone or in mixtures.

Exemplary monomers of Formula (10) and Formula (11) which can be employed in the process according to the present invention include divinylbenzene, divinyltoluene, divinylxylene, divinylethylbenzene, trivinylbenzene, divinyldiphenyl, divinyldiphenylmethane, divinyldibenzyl, divinylphenyl ether, divinyldiphenyl sulfide, divinyldiphenylamine, divinyl sulfone, divinyl ketone, divinylpyridine, diallyl phthalate, diallyl maleate, diallyl fumarate, diallyl succinate, diallyl oxalate, diallyl adipate, diallyl sebacate, diallylamine, triallylamine, N,N'-ethylenediacrylamide, N,N'-methylenediacrylamide, N,N'-methylenedimethacrylamide, ethylene glycol dimethacrylate, ethylene glycol diacrylate, 1,3-butylene glycol diacrylate and triallyl isocyanurate. These compounds may be used either alone or in mixtures.

The linear homopolymer, the linear copolymer or the cross-linked copolymer whose Z is a group of Formula (2), may also be prepared by the reaction of a polymer having vinylbenzaldehyde units and o-phenylenediamines of Formula (9).

As the starting material of this reaction, there may be mentioned a linear homopolymer comprising recurring units of Formula (13);

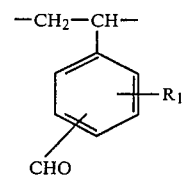

wherein $R_1$ is the same as defined above, a linear copolymer comprising about 98 to about 10 mol % of recurring units of Formula (13) and about 2 to about 90 mol % of recurring units of Formula (7) and a cross-linked copolymer comprising about 98 to about 10 mol % of recurring units of Formula (13), about 2 to about 50 mol % of either or both of the recurring units of Formula (5) and Formula (6) and 0 to about 88 mol % of recurring units of Formula (7).

As the o-phenylenediamine of Formula (9) there can be mentioned, for example, o-phenylenediamine, N-methyl-o-phenylenediamine, N-ethyl-o-phenylenediamine, N-propyl-o-phenylenediamine and N-benzyl-o-phenylenediamine. It may be used in the form of a salt such as a hydrochloric acid salt.

The molar ratio of o-phenylenediamine to a benzaldehyde group in these polymers is not critical, but is preferably 1 to 10.

The reaction temperature is not critical, but usually is in the range of from 0° C. to 150° C., preferably from 20° C. to 100° C.

The reaction time is not critical, but the reaction may usually be carried out for 30 minutes to 10 hours.

The reaction of the present invention may be carried out either in the presence or absence of an inert solvent, but, in the preparation of linear polymers, it is preferred that an inert solvent is used in a minimum amount necessary for providing a homogeneous system. In the process for the preparation of cross-linked copolymers, the inert solvent is preferably used in an amount of 1 ml/g to 1 l/g based on the weight of cross-linked polymer.

As the inert solvent, there can be mentioned, for example, water; aliphatic hydrocarbons such as pentane, hexane, heptane and octane; alcohols such as methanol, ethanol and isopropyl alcohol; ketones such as acetone, methyl ethyl ketone and diethyl ketone; ethers such as diethyl ether, methyl ethyl ether, dibutyl ether, diphenyl ether, dioxane and tetrahydrofuran; aromatic hydrocarbons such as benzene, toluene and xylenes; esters such as ethyl formate, ethyl acetate and butyl acetate; amides such as dimethyl formamide and dimethyl acetamide; halogenated aliphatic hydrocarbons such as chloroform, methylene chloride and dichloroethane; halogenated aromatic hydrocarbons such as chlorobenzene; and sulfoxides such as dimethyl sulfoxide. They may be used either alone or in mixtures.

It is preferred that a reaction promoter is added to the reaction system. The reaction promoter is a material which is able to increase the reaction rate by reacting with the benzaldehyde group in starting polymer or with the o-phenylenediamine.

The reaction promoter used in the present invention is the same as the compound used in the reaction of a vinylbenzaldehyde and an o-phenylenediamine as previously described.

The molar ratio of the reaction promotor to the amount of benzaldehyde group in starting polymer is usually 0.1 or more, preferably is 0.1 to 10, more preferably is 0.5 to 3.

The reaction promotor may be reacted previously with the benzaldehyde group in the starting polymer or the o-phenylenediamine, or it may be added to the mixture of starting polymer having vinylbenzaldehyde units and o-phenylenediamine.

The linear homopolymer, the linear copolymer or the cross-linked copolymer of this invention whose Z is a group of Formula (3) may be prepared by reacting the corresponding polymer whose Z is a group of Formula (2) with a compound $R_3Y$ ($R_3$ is the same as defined above and Y is a halogen atom).

The polymer of Formula (1) monomer wherein Z is a group of Formula (3) and at least one of $R_2$ and $R_3$ is a hydrogen atom, is an ammonium cation and can be prepared by the reaction of an acid and the corresponding polymer of Formula (1) monomer having a group of Formula (2) instead of a group of Formula (3). The molar ratio of the acid to the group of Formula (2) is usually one or more.

In this case, the conversion between a group of Formula (3) and a group of Formula (2) occurs reversibly by adding an acid or a base.

The polymer of Formula (1) monomer wherein Z is a group of Formula (3) and neither $R_2$ nor $R_3$ is a hydrogen atom, can be prepared by the reaction of the corresponding polymer having a group of Formula (2) instead of a group of Formula (3) and a compound represented by the formula $R_3Y$ ($R_3$ is as defined above and Y is a halogen atom). The molar ratio of the compound $R_3Y$ to the group of Formula (2) is preferably one or more, more preferably 1 to 10.

The polymer of Formula (1) monomer wherein Z is a group of Formula (3) and $R_2$ and $R_3$ are the same and not hydrogen atoms, can also be prepared by the reaction of a polymer of Formula (1) monomer wherein Z is a group of Formula (2) and $R_2$ is a hydrogen atom, and a compound represented by the formula $R_3Y$ (=$R_2Y$, $R_3$ is as defined above but not a hydrogen atom and Y is a halogen atom).

In this reaction, 2 moles of the compound of $R_3Y$ react with one mole of the group of Formula (2) in the polymer, theoretically. The amount of the compound $R_3Y$ is preferably 2 to 10 moles, per mole of the group of Formula (2).

In this case, a polymer of Formula (1) monomer wherein Z is a group of Formula (3) and at least one of $R_2$ and $R_3$ is a hydrogen atom, may be byproduced.

The conditions of the reaction of a polymer of Formula (1) monomer wherein Z is a group of Formula (2) and a compound $R_3Y$ described above are usually as follows.

The reaction temperature is not critical, but usually in the range of 20° C. to 150° C.

The reaction time is not critical, but the reaction may usually be carried out for 1 to 50 hours.

The reaction may be carried in the presence of an inert solvent.

As the inert solvent, there can be mentioned, for example, water; aliphatic hydrocarbons such as pentane, hexane, heptane and octane; alcohols such as methanol, ethanol and isopropyl alcohol; ketones such as acetone, methyl ethyl ketone and diethyl ketone; ethers such as diethyl ether, methyl ethyl ether, dibutyl ether, diphenyl ether, dioxane and tetrahydrofuran; aromatic hydrocarbons such as benzene, toluene and xylenes; esters such as ethyl formate, ethyl acetate and butyl acetate; amides such as dimethyl formamide and dimethyl acetamide; halogenated aliphatic hydrocarbons such as chloroform, methylene chloride and dichloroethane; halogenated aromatic hydrocarbons such as chlorobenzene; and sulfoxides such as dimethyl sulfoxide. They may be used either alone or in mixtures. In the preparation of linear polymers, it is preferred that the inert solvent is used in the minimum amount necessary for providing a homogeneous system. In the process for the preparation of cross-linked copolymer, the inert solvent is preferably used in an amount of 1 ml/g to 1 l/g based on the weight of cross-linked polymer.

In this reaction, a basic compound may be added to the reaction system. As the basic compound, there can be mentioned, for example, a salt of an alkali metal or an alkaline earth metal such as sodium hydroxide, potassium hydroxide and sodium carbonate and an alcoholate of an alkali metal or an alkaline earth metal such as sodium ethylate. The charging molar ratio of basic compound to group of Formula (2) in the starting polymer is not critical, but preferably is 0.1 to 10, more preferably 1 to 3.

In the case of preparing a polymer whose Z is a group of Formula (3) using a compound of Formula (1) wherein Z is a group of Formula (2) and $R_2$ is a hydrogen atom, the addition of the basic compound shows good results.

The polymer whose Z is a group of Formula (2) and $R_2$ is a hydrocarbon group or a carboxyalkyl group may also be prepared by reacting a halogenated hydrocarbon or a carboxyalkylhalide with a polymer whose Z is a group of Formula (2) and $R_2$ is a hydrogen atom.

In this case, the polymer whose Z is a group of Formula (3) is liable to be byproduced.

In accordance with a ninth aspect of the present invention, there is provided an ion exchange resin comprising cross-linked copolymer having about 10 to about 98 mol % of recurring units of Formula (4),

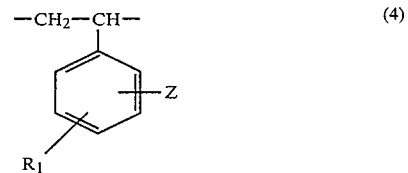

wherein Z and $R_1$ are the same as defined above.

The ion exchange resin of this invention may further have recurring units of Formula (5), Formula (6) or Formula (7).

The amount of the recurring unit of Formula (4) in the present ion exchange resin is about 10 to about 98 mol %, preferably about 30 to about 98 mol % based on the total moles of recurring units of the cross-linked copolymer.

As an example of this ion exchange resin, there may be mentioned a cross-linked copolymer comprising about 10 to about 98 mol % of the recurring units of Formula (4), about 2 to about 50 mol % of recurring units of Formula (5) and/or Formula (6), and 0 to about 88 mol % of recurring units of Formula (7).

Ion exchange can be effected with the novel ion exchange resin in conventional manner.

The ion exchange resin of this invention has excellent resistance to oxidation and chemicals as compared with known ion exchange resins.

The present invention will now be described in more detail with reference to the following examples which by no means limit the scope of the invention.

EXAMPLE 1

105.8 g of p-vinylbenzaldehyde, 400 ml of methanol and 400 ml of water were charged to a three-necked flask having a capacity of 200 ml and mixed to give a homogeneous solution. Then, 87 g of sodium hydrogensulfite was dissolved in 400 ml of water and this solution was charged dropwise to the above flask. Agitation was continued at room temperature for about 30 minutes. The resulting precipitate was separated by filtration, washed with methanol and then dried.

The amount of the product was 35.1 g.

23.6 g of this product, 10.0 g of o-phenylenediamine, 150 ml of dimethyl formamide and 0.1 g of t-butylcatechol were mixed and reacted for 1.5 hours at 50° C.

Then, 1N NaOH aqueous solution was added to the reaction mixture until a solution of PH10 was obtained.

The reaction mixture was left standing at −15° C. all day long.

The precipitated yellow crystals were separated by filtration, washed first with 18% aqueous sodium sulfite, then with 2% aqueous sodium sulfide and finally with water and then dried under reduced pressure. The amount of the product was 17.2 g.

The analysis results were as follows:
Elementary analysis:
C: 81.76 (81.79), H: 5.54 (5.49), N: 12.70 (12.72)

Each parenthetical figure shows a theoretical value.
Mass spectrum: 220 (M+/e), 193, 117, 103, 27, etc.

Nuclear magnetic resonance spectrum ($d_6$-DMSO, δ-value, ppm): 5.2∼6.0 (doublet, 2H) 6.5∼7.0 (double doublet, 1H) 7.1∼7.9 (multiplet, 9H)

The form of peak and the area of peak were shown in parentheses.

Infrared absorption spectrum ($cm^{-1}$): 3100, 1640, 1620, 1490, 1470, 1410, 1390, 1330, 1300, etc.

From the above results, the product was determined to be 2-(p-vinylphenyl)benzimidazole.

EXAMPLE 2

In substantially the same manner as in Example 1, using 12.2 g of N-methyl-o-phenylenediamine instead of o-phenylenediamine, the reaction was carried out. 21.3 g of the product was obtained using 23.6 g of the intermediate obtained by reacting p-vinylbenzaldehyde with sodium hydrogensulfite.

By spectroanalysis and other ordinary organic chemical analytic methods, it was determined that the substance was 1-methyl-2-(p-vinylphenyl)benzimidazole.

The analysis results were as follows:
Elementary analysis: C: 81.97 (82.02), H: 6.10 (6.02), N: 12.03 (11.96)

Each parenthetical figure shows a theoretical value.
Mass spectrum: 232 (M+/e), 217, 205, 129, 103, etc.

Nuclear magnetic resonance spectrum ($d_6$-DMSO, δ-value, ppm): 3.75 (singlet, 3H), 5.2∼6.0 (double doublet, 2H), 6.5∼7.0 (double doublet, 1H), 7.1∼7.9 (multiplet, 8H)

Infrared absorption spectrum ($cm^{-1}$): 3100, 1640, 1620, 1490, 1470, 1445, 1410, 1390, 1330, 1300, etc.

EXAMPLE 3

22.0 g of the product obtained in Example 1, 200 ml of dimethyl formamide and 0.1 g of t-butylcatechol were mixed and then 14.2 g of methyl iodide was added dropwise to the mixture under agitation.

The reaction mixture was poured into a large quantity of ether to precipitate the product. The precipitate thus obtained was separated by filtration and dissolved in 500 ml of 1N aqueous hydrochloric acid.

Then, the solution was neutralized with aqueous sodium hydroxide solution to obtain a precipitate.

This precipitated product was the same product obtained in example 2.

The yield was 45%.

EXAMPLE 4

In substantially the same manner as in Example 3, using 10.9 g of ethyl bromide or 12.7 g of benzyl chloride instead of methyl iodide, the reaction was carried out.

The analytical results were as follows.

(1) The product obtained using ethyl bromide:
Elementary analysis: (calc.) C: 82.32 (82.23), H: 6.40 (6.49), N: 11.28 (11.28)
Amount of C═C double bond: 4.03 mmol/g (2) The product obtained using benzyl chloride:
Elementary analysis: (calc.) C: 85.02 (85.13), H: 5.80 (5.84), N: 9.17 (9.03)
Amount of C═C double bond: 3.23 mmol/g The amounts of carbon-carbon double bond were measured by the method using bromine.

From the above results, the products were determined to be 1-ethyl-2-(p-vinylphenyl)benzimidazole and 1-phenylmethyl-2-(p-vinylphenyl)benzimidazole.

EXAMPLE 5

23.4 g of 1-methyl-2-(p-vinylphenyl)benzimidazole and 300 ml of dimethyl formamide were mixed, and then 27.4 g of butyl bromide was added dropwise to the mixture under agitation.

After reaction at 60° C. for 6 hours, the reaction mixture was poured into a large quantity of ether to precipitate the product. The precipitate thus obtained was separated by filtration and washed with ether.

The analytical results were as follows:
Elementary analysis: C: 64.60 (64.69), H: 6.34 (6.24), N: 7.60 (7.54) Br: 21.46 (21.52)

Each parenthetical figure showed a theoretical value.
Amount of carbon-carbon double bond: 2.70 mmol/g From the above results, the product was determined to be 1-methyl-2-(p-vinylphenyl)-3-butyl-benzimidazolium bromide.

In substantially the same manner as described above, using 25.3 g of benzyl chloride instead of butyl bromide, the reaction was carried out to obtain 1-methyl-2-(p-vinylphenyl)-3-benzylbenzimidazolium chloride.

The analytical results were as follows:
Elementary analysis (calc.): C: 76.64 (76.54), H: 5.93 (5.86) N: 7.62 (7.76), Cl: 9.81 (9.84)
Amount of C═C double bond: 2.87 mmol/g

EXAMPLE 6

16.0 g of 1-ethyl-3-vinyl-5-formylbenzene, 24.4 g of N-methyl-o-phenylenediamine, 10.4 g of sodium bisulfite, 0.05 g of t-butylcatechol and 100 ml of dimethyl formamide were charged to a flask having a capacity of 300 ml, mixed and reacted at 50° C. for 5 hours. 300 ml of 1N aqueous NaOH solution was added dropwise with stirring. The resulting precipitate was separated by filtration and washed adequately with water. The product was recrystallized from dimethyl acetamide. The yield was 5.0 g (19%).

The analytical results were as follows:

Elemetary analysis: C: 82.32 (82.41), H: 6.99 (6.92), N: 10.69 (10.68) Each parenthetical figure shows a theoretical value.

Mass spectrum: 262 (M+/e), 247, 235, 233, 132, 130, etc.

Nuclear magnetic resonance spectrum: 1.15 (triplet, 3H), 2.60 (quarter, 2H) 3.75 (singlet, 3H), 5.2~6.0 (double doublets, 2H), 6.5~7.0 (double doublet, 1H), 7.1~7.9 (multiplet, 7H)

Infrared absorption spectrum (cm$^{-1}$): 3100, 2950, 1640, 1620, 1490, 1475, 1450, 1385, 1330, 1300, 1260, 860, 760

From the above results, the product was determined to be 2-(3-ethyl-5-vinylphenyl)-1-methylbenzimidazole.

EXAMPLE 7

In a 300 ml three necked flask equipped with a thermometer, a gas inlet and a stirrer, 14.6 g of 1-vinyl-3-methyl-5-formylbenzene, 21.6 g of o-phenylenediamine, 0.05 g of tert-butylcatechol and 300 ml of dimethyl formamide were charged and stirred at 40° C. Sulfur dioxide was bubbled into this flask at the rate of 150 ml/min. After charging 12.8 g of sulfur dioxide, the reaction was continued for 6 hrs. at 40° C.

The resulting reaction mixture was pored into 1N-NaOH solution. The precipitate was filtered and redissolved in 300 ml dimethylformamide containing 10.2 g of sodium ethylate.

35 g of sodium chloroacatate was added dropwise to this solution, and the mixture was stirred for 6 hrs. at 40° C.

The precipitate from 1N-HCl was washed with methanol and dried.

The product was 8.4 g (Y=21%) and identified as 1.3-dicarboxymethyl-2-(3-vinyl-5-methylphenyl)benzimidazolium chloride from the following analysis.

Elementary analysis: C: 63.20 (63.24), H: 4.90 (4.80), N: 6.89 (7.02) O: 15.94 (16.05), Cl: 9.07 (8.88)

Basic exchange capacity: 2.51 meq/g

Cation exchange capacity: 5.00 meq/g

EXAMPLE 8

In substantially the same manner as in Example 6, using 13.2 g of vinylbenzaldehyde (m/p=6/4) and 19 g of sodium metabisulfite instead of 1-ethyl-3-vinyl-5-formylbenzene and sodium bisulfite, the reaction was carried.

The product was 1-methyl-2-(vinylphenyl)benzimidazole and the ratio of meta-isomer to para-isomer was 43/57, which was determined by gas chromatography.

EXAMPLE 9

20 g of HCl gas was bubbled into a solution comprising 11.0 g of the product obtained in Example 8 and 100 ml of methanol.

The product was obtained by recrystallization from ether.

From elementary analysis, the product was determined to be 1-methyl-2-(m/p-vinylphenyl)-3H-benzimidazolium chloride. Chlorine content was 13.22 (theoretical value is 13.09).

EXAMPLE 10

11.0 g of the product obtained in Example 8, 100 ml of methanol and 3.0 g of sodium methylate were charged to a flask having a capacity of 200 ml and stirred at 50° C. 21 g of methyliodide was added dropwise to the solution for about 30 minutes and reacted at 50° C. for 6 hours with stirring.

The reaction mixture was poured into water. The aqueous phase was washed three times with ether, and then concentrated to obtain a solid product. The product was purified by recrystallization from a mixture of water and methanol.

The yield was 15.1 g.

The elementary analytical results were as follows:

C: 54.18 (54.27), H: 4.63 (4.55) N: 7.45 (7.45), I: 33.74 (33.73)

From the above results, the product was determined to be 1,3-dimethyl-2-(m/p-vinylphenyl)benzimidazolium iodide.

EXAMPLE 11

An ampule having a capacity of 50 ml was charged with 5.0 g of 2-(p-vinylphenyl)benzimidazole, 40 ml of methanol and 0.05 g of azobisisobutyronitrile. After sufficiently shaking the ampule, the ampule was purged with nitrogen and sealed. Then the ampule was kept in an oil bath maintained at 90° C. for 18 hours. After cooling the ampule, the ampule was broken off and the contents were mixed with n-hexane, followed by filtration to obtain a precipitate. The precipitate was washed with n-hexane and dried under reduced pressure to obtain 4.7 g (94%) of a pale yellow product.

Elementary analysis of the product thus obtained gave the following results:

C: 81.52 (81.79), H: 5.62 (5.49), N: 12.86 (12.72)

Each parenthetical figure shows a theoretical value.

Main absorption peaks in an infrared spectrum of the product were as follows:

3100, 2950, 1620, 1490, 1470, 1410, 1390, 1330, 1300, etc. (unit: cm$^{-1}$)

As is apparent from the main absorption peaks, the absence of carbon-carbon double bond implied by the lack of peaks near the frequency 1640 cm$^{-1}$ showed the formation of a polymer.

The number-aveerage molecular weight of the obtained polymer measured by gel permeation chromatography was 600,000.

1 g of the polymer thus obtained and 0.14 g of cupric chloride were dissolved in 2N hydrochloric acid to prepare a solution having a total volume of 50 ml. After the solution was extracted with five 50 ml portions of chloroform, the cupric concentration of the aqueous phase was measured. As a result, the cupric concentration was found to be 2 mmole/liter. From the above result, it was found that the polymer can be used as an extractant of metals.

EXAMPLES 12 TO 20

In substantially the same manner as in Example 11, various linear homopolymers of Formula (4) were synthesized. The materials, experimental conditions and the analytical results are summarized in Table 1.

TABLE 1

| Ex. No. | R₁ | Z | R₂ | R₃ | X | Weight (g) | Initiator*² | Inert*³ solvent | Polymerization conditions Temp. × Time | Treat-*⁴ ment/ | Yield (%) | Molecular weight (Mn) | Elementary analysis (calc.) |
|---|---|---|---|---|---|---|---|---|---|---|---|---|---|
| 12 | H | p- | Me | | | 10.0 | AIBN 0.1 g | methanol | 90° C. × 18 hr. | H | 95 | 700,000— | C: 81.89 (82.02) H: 6.00 (6.02) N: 12.11 (11.96) |
| 13 | H | p- | Et | | | 10.0 | AIBN 0.1 g | methanol | 90° C. × 18 hr. | H | 99 | 700,000— | C: 82.19 (82.23) H: 6.54 (6.49) N: 11.27 (11.28) |
| 14 | H | p- | Bz | | | 10.0 | AIBN 0.1 g | methanol | 90° C. × 18 hr. | H | 100 | 400,000— | C: 84.99 (85.13) H: 5.90 (5.84) N: 9.11 (9.03) |
| 15 | 3-Et | 5- | Me | | | 10.0 | AIBN 0.1 g | methanol | 90° C. × 18 hr. | H | 95 | 600,000— | C: 82.42 (82.41) H: 6.98 (6.92) N: 10.60 (10.68) |
| 16 | H | m/p = 5/5 | Me | | | 10.0 | AIBN 0.1 g | methanol | 90° C. × 18 hr. | H | 97 | 900,000 | C: 81.96 (82.02) H: 6.02 (6.02) N: 12.02 (11.96) |
| 17 | H | p- | Me | Me | Cl | 10.0 | BPO 0.1 g | DMAc | 100° C. × 20 hr. | H | 100 | 200,000— | C: 71.63 (71.70) H: 6.08 (6.02) N: 9.75 (9.84) Cl: 12.54 (12.45) |
| 18 | H | p- | Me | Bu | Br | 10.0 | AIBN 0.1 g | DMAc | 100° C. × 20 hr. | H | 100 | 400,000— | C: 64.75 (64.69) H: 6.28 (6.24) N: 7.59 (7.54) Br: 21.38 (21.52) |
| 19 | H | p- | Me | Bz | Cl | 10.0 | AIBN 0.1 g | DMF | 100° C. × 20 hr. | H | 100 | 400,000— | C: 76.55 (76.55) H: 5.94 (5.86) N: 7.67 (7.76) Cl: 9.84 (9.82) |
| 20 | H | p- | H | Me | Cl | 10.0 | AIBN 0.1 g | DMF | 100° C. × 20 hr. | H | 100 | 400,000— | C: 71.02 (70.98) H: 5.62 (5.58) N: 10.09 (10.35) Cl: 13.27 (13.09) |

*¹Me — methyl
Et — ethyl
Bz — benzyl
Bu — butyl
*²AIBN — azobisisobutyronitrile
BPO — benzoyl peroxide
*³DMAc — dimethyl acetamide
DMF — dimethyl formamide
*⁴H — Recovered from hexane

EXAMPLE 21

11.0 g of 2-(p-vinylphenyl)benzimidazole, 5.2 g of styrene and 0.1 g of azobisisobutyronitrile were placed in an ampule having a capacity of 50 ml. After shaking the ampule, the ampule was purged with nitrogen and sealed. The ampule was then kept in a water bath maintained at 90° C. for 18 hours. Then the ampule was broken off and the solidified contents were taken out. With respect to the product thus obtained, elementary analysis and infrared analysis were carried out. The results were as follows:

Elementary analysis: C: 85.05 (85.15), H: 6.22 (6.21), N: 8.73 (8.63)

Each parenthetical figure shows a theoretical value.

Infrared absorption spectrum (cm⁻¹): 3400, 3050, 1620, 1600, 1490, 1450, 1280, 740, 700, etc.

The obtained solid product amounted to 16.2 g (yield: 100%). When 0.5 g of the obtained solid product was mixed with 100 ml of 2N hydrochloric acid, the product was completely dissolved in the hydrochloric acid solution and no oily liquid appeared on the surface of the hydrochloric acid solution at all.

Judging from both the infrared adsorption spectrum of the product which indicated the lack of peaks due to carbon-carbon double bond and the result of the above-mentioned dissolving test using a hydrochloric acid solution, the product was concluded to be a 2-(p-vinylphenyl)benzimidazole-styrene copolymer.

The number-average molecular weight of this polymer, which was measured by gel permeation chromatography using polystyrene as a standard material, was 1,200,000.

1 g of the obtained copolymer and 0.270 g of ferric chloride (FeCl₃.6H₂O) were dissolved in 2N hydrochloric acid to prepare a solution having a total volume of 50 ml. After the solution was extracted with five 50 ml portions of chloroform, the concentration of iron contained in the hydrochloric acid solution was measured. As a result, the iron concentration was found to be 1 mmole/liter. Substantially the same procedures as mentioned above were repeated to prepare a solution of ferric chloride in hydrochloric acid except that none of the polymer was added. The solution so prepared was extracted with five 50 ml portions of chloroform. After extraction, the concentration of iron in the water phase was measured. As a result, the iron concentration was found to be 19 mmole/liter. The iron concentration was nearly equal to the concentration before extraction. From the above results, it was found that the polymer can be used as an extractant of metals.

EXAMPLES 22 TO 35

In substantially the same manner as in Example 21, using a monomer of Formula (1) and a monomer of Formula (12), copolymerization were carried out. The materials, experimental conditions and the analysis are summarized in Table 2.

TABLE 2

| Ex. No. | Compound (1)*1 R₁ | Z | R₂ | R₃ | X | Weight (g) | Compound (12) Compound name | Weight (g) | Initiator*2 | Inert*3 solvent | Polymerization conditions Temp. × Time | Yield (%) | Molecular weight (Mn) | Elementary analysis*4 (calc.) |
|---|---|---|---|---|---|---|---|---|---|---|---|---|---|---|
| 22 | H | p- | Me | — | — | 9.4 | styrene | 4.16 | AIBN 0.1 g | methanol 50 ml | 90° C. × 18 hr. | 100 | 1000000 | C: 85.12 (84.92)<br>H: 6.77 ( 6.83)<br>N: 8.11 ( 8.25) |
| 23 | H | m/p- (m/p = 6/4) | Me | Me | Cl | 22.76 | vinyl acetate | 1.72 | AIBN 0.1 g | methanol 50 ml | 90° C. × 18 hr. | 95 | 400000 | C: 70.25 (70.58)<br>H: 6.24 ( 6.09)<br>N: 9.00 ( 9.15)<br>O: 2.70 ( 2.61)<br>Cl: 11.81 (11.57) |
| 24 | Et | p- | Bu | — | — | 9.06 | acrylonitrile | 1.06 | AIBN 0.1 g | DMF 50 ml | 90° C. × 18 hr. | 95 | 70000 | C: 81.72 (81.78)<br>H: 7.32 ( 7.16)<br>N: 10.96 (11.06) |
| 25 | H | p- | Me | Bz | Cl | 7.21 | methyl acrylate | 6.88 | AIBN 0.1 g | DMF 50 ml | 90° C. × 18 hr. | 98 | 300000 | C: 66.56 (66.42)<br>H: 6.51 ( 6.43)<br>N: 3.82 ( 3.97)<br>O: 18.13 (18.15)<br>Cl: 4.98 ( 5.03) |
| 26 | H | m/p- (m/p = 6/4) | Me | — | — | 7.05 | methacrylic acid | 6.02 | AIBN 0.1 g | DMF 50 ml | 90° C. × 18 hr. | 96 | 400000 | C: 69.82 (69.76)<br>H: 6.59 ( 6.70)<br>N: 6.55 ( 6.42)<br>O: 17.04 (17.12) |
| 27 | H | p- | Me | Bu | Br | 14.84 | methyl methacrylate | 6.0 | AIBN 0.1 g | DMF 50 ml | 90° C. × 18 hr. | 98 | 600000 | C: 63.71 (63.34)<br>H: 6.88 ( 6.76)<br>N: 5.31 ( 5.37)<br>O: 9.01 ( 9.20)<br>Br: 15.09 (15.32) |
| 28 | H | p- | Me | — | — | 14.1 | methylvinyl ketone | 2.8 | BPO 0.1 g | methanol 50 ml | 90° C. × 18 hr. | 97 | 40000 | C: 79.46 (79.50)<br>H: 6.79 ( 6.79)<br>N: 9.84 ( 9.93)<br>O: 3.91 ( 3.78) |
| 29 | H | p- | H | — | — | 15.4 | vinylidene chloride | 2.91 | AIBN 0.1 g | methanol 50 ml | 90° C. × 18 hr. | 95 | 30000 | C: 72.73 (72.74)<br>H: 4.99 ( 4.95)<br>N: 10.69 (10.70)<br>Cl: 11.59 (11.61) |
| 30 | H | m/p- (m/p = 6/4) | Me | Me | Cl | 14.23 | vinyltoluene | 5.9 | AIBN 0.1 g | DMF 50 ml | 90° C. × 18 hr. | 100 | 900000 | C: 77.51 (77.50)<br>H: 6.84 ( 6.75)<br>N: 7.02 ( 6.95)<br>Cl: 8.63 ( 8.80) |
| 31 | H | m/p- (m/p = 6/4) | Me | Me | Cl | 14.23 | chlorostyrene | 6.93 | AIBN 0.1 g | DMF 50 ml | 90° C. × 18 hr. | 100 | 900000 | C: 70.88 (70.92)<br>H: 5.76 ( 5.71)<br>N: 6.54 ( 6.62)<br>Cl: 16.82 (16.75) |
| 32 | H | m/p- (m/p = 6/4) | Me | — | — | 18.8 | chloromethylstyrene | 3.05 | AIBN 0.1 g | methanol 50 ml | 90° C. × 18 hr. | 100 | 1400000 | C: 80.04 (80.16)<br>H: 6.31 ( 6.36)<br>N: 10.03 (10.24)<br>Cl: 3.61 ( 3.24) |
| 33 | H | p- | Me | — | — | 18.8 | vinylimidazole | 1.88 | AIBN 0.1 g | methanol 50 ml | 90° C. × 18 hr. | 99 | 60000 | C: 79.94 (80.05)<br>H: 6.61 ( 6.43)<br>N: 13.45 (13.53) |
| 34 | H | p- | Me | Et | Br | 24.0 | vinylpyridine | 3.9 | AIBN 0.1 g | DMF 50 ml | 90° C. × 18 hr. | 100 | 1000000 | C: 65.67 (65.79)<br>H: 5.72 ( 5.66)<br>N: 8.47 (8.52)<br>Br: 20.14 (20.02) |
| 35 | H | p- | Me | Et | Br | 6.86 | vinylcarbazole | 3.86 | AIBN 0.1 g | DMF 50 ml | 90° C. × 18 hr. | 92 | 40000 | C 71.59 (71.64)<br>H: 5.57 ( 5.64)<br>N: 7.68 ( 7.83)<br>Br: 15.16 (14.89) |

*1Me; methyl, Et; ethyl, Bu; butyl, Bz; benzyl,
*2BPO; benzoyl peroxide, AIBN; azobisisobutylonitrile,
*3DMF; dimethyl formamide
*4The parenthetical figure is calculated on the assumption that mole fraction of copolymer is the same as that of monomer. The similarity between the calculated and observed data indicates that the mole fraction of copolymer is substantially the same as that of monomer.

EXAMPLE 36

13.56 g of the polymer obtained in Example 22 was dissolved in 1 l of methanol. To the solution, 2.72 g of sodium ethylate was added and mixed at 50° C. Then, 11.4 g of methyl iodide was added dropwise to the mixture during 30 minutes and reacted at 50° C. for 5 hours with stirring.

The reaction mixture was poured into ether to recover a product.

The product was dried under reduced pressure.

After treating a part of the product with a large volume of aqueous HCl solution, the amount of strong basic groups was measured by conventional method. The result was 2.57 meq/g.

The content of iodide of the product was 26.4% by weight.

From the above results, it was found that all benzimidazole groups of the polymer were converted to form 1,3-dimethyl-benzimidazolium iodide groups.

TABLE 3

| Ex. No. | Compound (1)*1 Z | R1 | R2 | R3 | X | Weight (g) | Compound (10) or Compound (11) Weight (g) | Compound (12) Weight (g) | Initiator*2 | Inert*3 solvent | Polymerization conditions Temp. × Time | Yield (%) | Exchange capacity (meq/g) (Calc.) | Elementary analysis*4 (Calc.) |
|---|---|---|---|---|---|---|---|---|---|---|---|---|---|---|
| 38 | p- | H | Me | — | — | 18.8 | triallyl isocyanurate 4.98 | — | AIBN 0.1 g | methanol 50 ml | 90° C. × 18 hr. | 97 | 3.05 (3.00) | C: 76.61 (76.68) H: 6.48 (6.35) N: 12.91 (12.94) O: 4.00 (4.03) |
| 39 | m/p- m/p = 6/4 | H | Me | Me | Cl | 22.76 | m-divinylbenzene 2.6 | — | AIBN 0.1 g | DMF 50 ml | 90° C. × 18 hr. | 100 | 3.10 (3.15) | C: 74.04 (73.81) H: 6.17 (6.19) N: 8.72 (8.83) Cl: 11.08 (11.17) |
| 40 | p- | Et | Bu | — | — | 24.16 | p,p'-divinylbiphenyl 2.06 | styrene 1.04 | AIBN 0.1 g | methanol 50 ml | 90° C. × 18 hr. | 100 | 2.66 (2.65) | C: 86.46 (86.47) H: 7.43 (7.42) N: 6.11 (6.11) |
| 41 | p- | H | Me | Bz | Cl | 25.24 | 1,2-di(vinylphenyl)-ethane 4.14 | — | AIBN 0.1 g | DMF 50 ml | 90° C. × 18 hr. | 100 | 2.37 (2.38) | C: 78.05 (78.01) H: 6.81 (6.89) N: 6.60 (6.67) Cl: 8.54 (8.44) |
| 42 | m/p- m/p = 6/4 | H | Me | — | — | 21.15 | divinylphenyl-ether 2.22 | — | AIBN 0.1 g | methanol 50 ml | 90° C. × 18 hr. | 100 | 3.38 (3.38) | C: 82.14 (82.12) H: 6.42 (6.42) N: 10.74 (10.77) O: 0.70 (0.68) |
| 43 | p- | H | Me | Bu | Br | 33.38 | divinylphenyl-amine 2.21 | — | AIBN 0.1 g | DMAc 50 ml | 90° C. × 18 hr. | 96 | 3.11 (3.11) | C: 66.24 (66.07) H: 6.34 (6.28) N: 7.25 (7.47) Br: 20.17 (20.18) |
| 44 | p- | H | Me | — | — | 22.35 | diallyl terephthalate 0.95 | — | AIBN 0.1 g | ethanol 50 ml | 90° C. × 17 hr. | 95 | 3.54 (3.55) | C: 81.55 (81.43) H: 6.43 (6.47) N: 11.30 (11.42) O: 0.72 (0.69) |
| 45 | p- | H | H | — | — | 15.4 | ethylene glycol dimethacrylate 3.0 | methyl methacrylate 1.5 | AIBN 0.1 g | ethanol 50 ml | 90° C. × 18 hr. | 94 | 3.10 (3.12) | C: 76.95 (76.86) H: 6.04 (6.07) N: 9.81 (9.84) O: 7.20 (7.23) |
| 46 | m/p- m/p = 6/4 | H | Me | Me | Cl | 22.76 | methylenebis-acrylamide 1.54 | acrylamide 0.71 | AIBN 0.1 g | DMF 50 ml | 90° C. × 18 hr. | 97 | 3.19 (3.20) | C: 69.85 (70.04) H: 6.24 (6.08) N: 10.54 (10.63) O: 1.89 (1.92) Cl: 11.48 (11.33) |
| 47 | m/p- m/p = 6/4 | H | Me | Me | Cl | 17.07 | divinyl-pyridine 5.24 | — | AIBN 0.1 g | DMF 50 ml | 90° C. × 18 hr. | 99 | 4.21 (4.21) | C: 74.41 (74.21) H: 6.52 (6.23) N: 9.69 (10.03) |
| 48 | m/p- m/p = 6/4 | H | Me | — | — | 18.8 | triallylamine 2.74 | — | AIBN 0.1 g | methanol 50 ml | 90° C. × 18 hr. | 95 | 3.96 (3.97) | C: 81.73 (81.67) H: 6.55 (6.42) N: 9.38 (9.52) |
| 49 | p- | H | Me | — | — | 14.1 | trivinyl-benzene 3.12 | divinyl-benzene 2.6 | AIBN 0.1 g | methanol 50 ml | 90° C. × 18 hr. | 100 | 2.75 (2.73) | C: 84.82 (84.73) H: 6.75 (6.81) N: 11.72 (11.90) |
| 50 | p- | H | Me | Et | Br | 30.86 | diallyl maleate 1.96 | — | AIBN 0.1 g | DMF 50 ml | 90° C. × 18 hr. | 94 | 3.14 (3.12) | C: 63.17 (62.88) H: 5.71 (5.61) N: 8.43 (8.47) O: 7.58 (7.67) |

EXAMPLE 37

An ampule having a capacity of 100 ml was charged with 14.15 g of 2-(p-vinylphenyl)benzimidazole, 4.67 g of commercially available divinylbenzene having a purity of 56%, 30 ml of methanol and 0.1 g of azosisobutyronitrile. After sufficiently shaking the ampule, the ampule was purged with nitrogen and heat-sealed. Then the ampule was kept in a water bath maintained at 90° C. for 18 hours. Then the ampule was broken off and the contents were taken out and washed with water and acetone.

Elemetary analysis of the product thus obtained gave the following results:

C: 84.08 (84.24), H: 6.32 (6.20), N: 9.60 (9.56) Each parenthetical figure shows a theoretical value.

Main absorption peaks in an infrared absorption spectrum of the product were as follows:

3400, 3050, 1620, 1600, 1490, 1450, 1280, 740, 700, etc. (unit: $cm^{-1}$)

The obtained solid product was quite insoluble in acetone. The yield was 100%. In the infrared absorption spectrum, the peaks due to the carbon-carbon double bond of the monomer material disappeared. From the abovementioned analysis, this product was concluded to be a cross-linked copolymer of 2-(p-vinylphenyl)benzimidazole, divinylbenzene and ethylstyrene.

This polymer was found to have 3.04 meq./g of exchange capacity measured by known method.

EXAMPLES 38 TO 51

In substantially the same manner as in Example 37, using a monomer of Formula (1), a monomer of Formula (12) and a monomer of Formula (10) or a monomer of Formula (11), various kinds of cross-linked copolymers were synthesized. The materials, experimental conditions and the analytical results are summarized in Table 3.

TABLE 3-continued

| Ex. No. | Compound (1)[*1] | | | | | | Compound (12) Weight (g) | Compound (10) or Compound (11) Weight (g) | Initi-[*2] ator | Inert[*3] solvent | Polymerization conditions Temp. × Time | Yield (%) | Exchange capacity (meq/g) (Calc.) | Elementary analysis[*4] (Calc.) |
| --- | --- | --- | --- | --- | --- | --- | --- | --- | --- | --- | --- | --- | --- | --- |
| | R₁ | Z | R₂ | R₃ | X | Weight (g) | | | | | | | | |
| 51 | H | p- | Me | Et | Br | 18.86 | — | divinylketone 3.69 | AIBN 0.1 g | DMF 50 ml | 90° C. × 18 hr. | 96 | 2.74 (2.74) | O: 1.87 (1.95)<br>Br: 21.67 (21.89)<br>C: 65.05 (64.65)<br>H: 5.96 (5.87)<br>N: 6.80 (6.83)<br>O: 3.17 (3.19)<br>Br: 19.02 (19.47) |

[*1]Me; methyl, Et; ethyl, Bu; butyl, Bz, benzyl,
[*2]AIBN; azobisisobutyronitrile,
[*3]DMF; dimethyl formamide, DMAc; dimethyl acetamide
[*4]The parenthetical figure is calculated on the assumption that mole fraction of copolymer is the same as that of monomer. The similarity between the calculated and observed data indicates that the mole fraction of copolymer is substantially the same as that of monomer.

EXAMPLE 52

100 g of the cross-linked copolymer comprising 80 mol % of vinylbenzaldehyde (m/p=6/4) and 20 mol % of meta-divinylbenzene, 1 l of dimethyl acetamide and 196 g of o-phenylenediamine were charged to a three-necked flask equipped with a stirrer having a capacity of 2 l. After 78 g of sulfur dioxide gas was bubbled into the mixture at 60° C. for 30 minutes, the mixture was stirred at 60° C. for 6 hours.

The product was separated by filtration and washed with 0.1N aqueous NaOH solution, then with water and at last with acetone.

The analytical results were as follows:
Elementary analysis: C: 82.66, H: 5.88, N: 9.97, O: 1.49
Infrared absorption spectrum (cm$^{-1}$): 3400, 3050, 1700, 1620, 1600, 1490, 1450, 1280, 1100, 740, 700, etc.
Exchange capacity: 3.15 meq/g From the above results, it was found that the product was a polymer comprising 20 mol % of meta-divinylbenzene, 69 mol % of 2-(m/p-vinylpheny)benzimidazole, 7 mol % of vinylbenzoic acid and 4 mol % of vinylbenzylalcohol.

EXAMPLE 53

13.2 g of a cross-linked copolymer comprising 80 mol % of vinylbenzaldehyde (m/p=6/4) unit and 20 mol % of m-divinylbenzene unit was dispersed in 100 ml of dimethyl formamide, then 25 g of a salt of sulfurous acid with N-methyl-o-phenylenediamine was added to the dispersion and the resulting mixture was reacted at 90° C. for 6 hours with stirring.

The analytical results were as follows:
Elementary analysis: C: 81.51, H: 6.80, N: 10.60, O: 1.09
Anionic exchange capacity: 3.29 meq/g
Weakly cationic exchange: 0.19 meq/g From the above results, the product was determined to be a copolymer comprising 20 mol % of m-divinylbenzene units, 70 mol % of 2-(m/p-vinylphenyl)-1-methylbenzimidazole units, 4 mol % of vinylbenzoic acid units and 6 mol % of divinylbenzyl alcohol units.

EXAMPLE 54

10 g of the product obtained in example 53 was dispersed in 100 ml of methanol.

The dispersion was charged to an autoclave with methyl chloride gas, the mixture was reacted at 60° C. under a gauge pressure of 3 Kg/cm$^2$ for 20 hours under agitation.

The strongly anionic capacity and the total basic capacity of the product were 2.60 meq/g and 3.17 meq/g respectively.

From the above results, it was found that 82% of 2-(m/p-vinylphenyl)-1-methylbenzimidazole units in the starting polymer was converted to 1,3-dimethyl-2-(m/p-vinylphenyl)-benzimidazolium chloride units.

The results of elementary analysis supported the above result.

EXAMPLE 55

20.65 g of a cross-linked copolymer comprising 15 mol % of recurring units of m-divinylbenzene and 85 mol % of recurring units of 2-vinylphenylbenzimidazale (m/p=6/4) was dispersed in a mixed solvent consisting of 150 ml of water and 150 ml of methanol. Then, 30.7 g of sodium chloroacetate and 3.4 g of sodium hydroxide were added to the dispersion and the mixture thus obtained was refluxed for 18 hours with stirring.

The product was separated by filtration and washed with a dilute aqueous hydrochloric acid solution and then with water.

The exchange capacities of the product were as follows:
Total anionic exchange capacity; 2.70 meq/g
Strongly anionic exchange capacity; 1.70 meq/g
Weakly cationic exchange capacity; 4.22 meq/g;

From the above results, it was found that 63% of the recurring units of 2-vinylphenylbenzimidazole in the starting polymer was converted to recurring units of 1,3-dicarboxymethyl-2-vinylphenylbenzimidazolium chloride and 30% of that was converted to recurring units of 1-carboxymethyl-2-vinylphenylbenzimidazole.

EXAMPLE 56

20.65 g of the same polymer as used in Example 55 was dispersed in 300 ml of methanol. Then, 6.6 g of sodium ethylate was added to the dispersion and the mixture was refluxed with stirring. With refluxing, 72.4 g of methyl iodide was added dropwise to the mixture and this mixture was further refluxed for 8 hours with stirring.

The product was separated by filtration and washed with methanol and then with water.

The total anionic exchange capacity and strongly anionic exchange capacity were 3.29 meq/g and 3.03 meq/g respectively.

From the above results, it was found that 92% of the recurring units of 2-vinylphenylbenzimidazole was converted to units of 1,3-dimethyl-2-vinylphenylbenzimidazolium iodide and 6% of that was converted to units of 1-methyl-2-vinylphenylbenzimidazole.

EXAMPLE 57

Various kinds of cross-linked copolymers having recurring units of Formula (4) were synthesized as shown in Table 4.

TABLE 4

| | | | Composition of copolymer | | | | | | | | |
|---|---|---|---|---|---|---|---|---|---|---|---|
| | | | | Compound (1) | | | | | | | |
| No. | Crosslinkable monomer*[1] | | $R_1$ | Z | $R_2$ | $R_3$ | X | mol %*[2] | Another monomer*[3] | | |
| 1 | m-DVB | 15 mol % | H | p- | H | — | — | 55 | St | | 30 mol % |
| 2 | m/p-DVB (m/p = 7/3) | 20 mol % | H | p- | Me | — | — | 34 | m/p-ES | (m/p = 7/3) | 16 mol % |
| | | | | | | | | | St | | 30 mol % |
| 3 | m-DVB | 20 mol % | H | m/p- | Me | — | — | 22 (m/p = 6/4) | m/p-VBA | (m/p = 6/4) | 8 mol % |
| 4 | DVT | 35 mol % | H | m/p- | Me | Me | Cl | 50 (m/p = 6/4) | | | |
| | | | 3-Et | 5- | Me | Bz | Cl | 65 | | | |

TABLE 4-continued

| | | Composition of copolymer | | | | | | | |
|---|---|---|---|---|---|---|---|---|---|
| | | | Compound (1) | | | | | | |
| No. | Crosslinkable monomer*1 | | R1 | Z | R2 | R3 | X | mol %*2 | Another monomer*3 |
| 5 | m/p-DVB (m/p = 7/3) | 5 mol % | H | m/p- | Bu | Me | Cl | 91 (m/p = 6/4) | m/p-ES (m/p = 7/3) 4 mol % |

*1DVB: divinylbenzene
DVT: divinyltoluene
*2Me: methyl
Bu: butyl
Bz: benzyl
*3St: styrene
Es: ethylstyrene
VBA: vinylbenzoic acid A cylindrical glass column having an inner diameter of 10 mm equipped with a filter and a cock were packed with 10 ml of the copolymer, Sample No. 1, shown in Table 4.

After packing, 200 ml of 1N aqueous HNO3 solution, and then 100 ml of acetone were passed through the column. Then, the copolymer was removed from the column, dried and dipped in 50 ml of 0.2 mol/l of aqueous KI solution over night.

After separation of the copolymer by filtration, the amount of chlorine ion in the filtrate was measured.

The result was 37 mmol.

Regarding Sample No. 2, the same procedure as described above was repeated and the result was 91 mmol.

Further, the procedure was repeated substantially in the same manner except for using the copolymer of Sample No. 3, No. 4 or No. 5 and passing 1N aqueous HNO3 solution through the column until chloride ion was not detected in the effluent from the bottom of each column.

The amount of chlorine ion of each effluent obtained by using the copolymer of Sample No. 3, No. 4 and No. 5 was 38 mmol, 77 mmol and 41 mmol.

From the above results, it was found that the copolymers of Samples No. 1 to No. 5 could be used as anion exchange resins.

It is understood that the specification and examples are illustrative but not limitative of the present invention and that other embodiments within the spirit and scope of the invention will suggest themselves to those skilled in the art.

What is claimed is:

1. A basic compound of Formula (1):

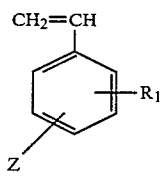

(1)

wherein $R_1$ is a hydrogen atom or a straight chain or branched hydrocarbon group having 1 to 4 carbon atoms, and Z is a group of Formula (2) or Formula (3):

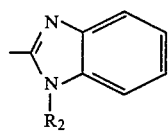

(2)

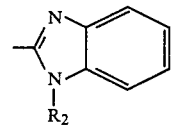

(3)

wherein $R_2$ and $R_3$ each independently is a hydrogen atom, a straight chain or branched hydrocarbon group having 1 to 10 carbon atoms or a carboxyalkyl group having 2 to 10 carbon atoms.

2. A basic compound as claimed in claim 1, wherein $R_1$ is a hydrogen atom, a methyl group or an ethyl group.

3. A basic compound as claimed in claim 1, wherein $R_2$ and $R_3$ each independently is a hydrogen atom, a methyl group, an ethyl group, a benzyl group or a carboxymethyl group.

4. A basic polymer comprising about 10 to 100 mol % of recurring units of Formula (4):

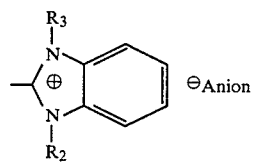

(4)

wherein $R_1$ is a hydrogen atom or a straight chain or branched hydrocarbon group having 1 to 4 carbon atoms, Z is a group of Formula (2) or Formula (3):

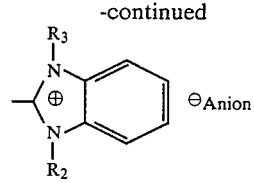

(2)

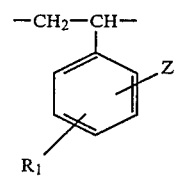

(3)

wherein $R_2$ and $R_3$ each independently is a hydrogen atom, a straight chain or branched hydrocarbon group having 1 to 10 carbon atoms or a carboxyalkyl group having 2 to 10 carbon atoms, 0 to about 50 mol % of recurring units of Formula (5) plus Formula (6):

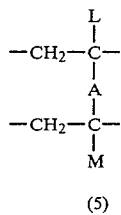 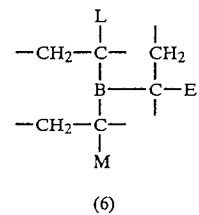

(5) (6)

wherein L, M and E each independently is a hydrogen atom or a methyl group; A is

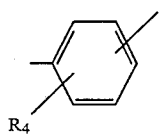

wherein $R_4$ is a hydrogen atom or a $C_1$–$C_5$ hydrocarbon residue;

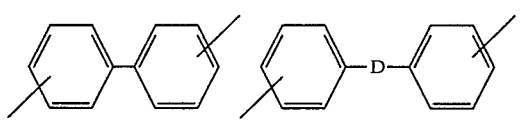

wherein D is —O—, —S—, —NH— or a divalent $C_1$–$C_5$ hydrocarbon residue;

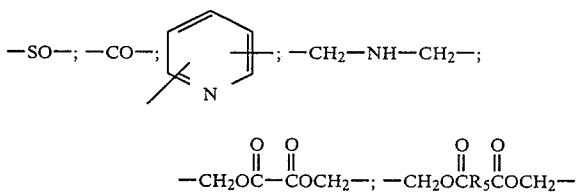

wherein $R_5$ is a divalent $C_1$–$C_8$ hydrocarbon residue;

wherein $R_6$ is a divalent $C_1$–$C_5$ hydrocarbon residue; or

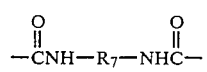

wherein $R_7$ is a divalent $C_1$–$C_3$ hydrocarbon residue; and B is

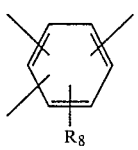

wherein $R_8$ is a hydrogen atom or a $C_1$–$C_5$ hydrocarbon residue;

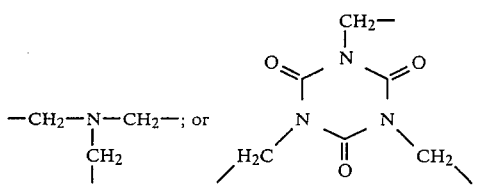

and 0 to about 88 mol % of recurring units of Formula (7):

wherein P and Q each independently is a hydrogen atom, a halogen atom, a cyano group, an aryl group, a halogenophenyl group, a phenyl group substituted with one or more substituents selected from $C_1$–$C_5$ straight chain or branched alkyl and haloalkyl groups, —COOR$_9$ in which R$_9$ is a hydrogen atom or R$_{10}$, R$_{10}$ is a $C_1$–$C_{10}$ hydrocarbon residue, —COR$_9$, —OCOR$_{10}$, —CONHR$_9$, an imidazolyl group, a pyridyl group and a carbazolyl group, based on the total moles of recurring units of Formula (4), Formula (5), Formula (6) and Formula (7).

5. A linear homopolymer comprising recurring units of Formula (4):

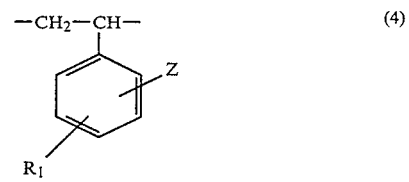

wherein $R_1$ is a hydrogen atom or a straight chain or branched hydrocarbon group having 1 to 4 carbon atoms, and Z is a group of Formula (2) or Formula (3):

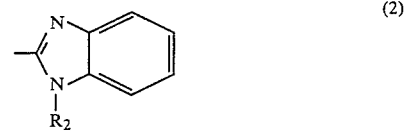

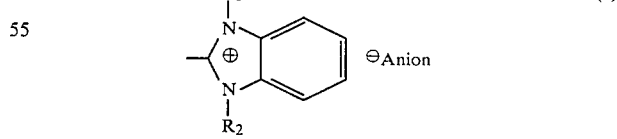

wherein $R_2$ and $R_3$ each independently is a hydrogen atom, a straight chain or branched hydrocarbon group having 1 to 10 carbon atoms or a carboxyalkyl group having 2 to 10 carbon atoms, having a number-average molecular weight of about 1,000 to about 2,000,000.

6. A linear homopolymer as claimed in claim 5, wherein $R_1$ is a hydrogen atom, a methyl group or an ethyl group.

7. A linear homopolymer as claimed in claim 5, wherein $R_2$ and $R_3$ each independently is a hydrogen atom, a methyl group, an ethyl group, a benzyl group or a carboxymethyl group.

8. A linear copolymer comprising about 98 to about 10 mol % of recurring units of Formula (4):

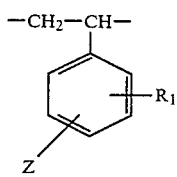
(4)

wherein $R_1$ is a hydrogen atom or a straight chain or branched hydrocarbon group having 1 to 4 carbon atoms, and Z is a group of Formula (2) or Formula

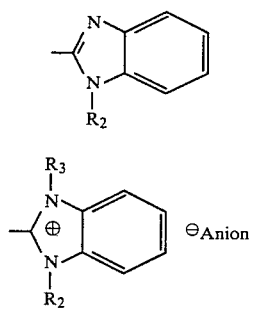
(2)
(3)

wherein $R_2$ and $R_3$ each independently is a hydrogen atom, a straight chain or branched hydrocarbon group having 1 to 10 carbon atoms or a carboxyalkyl group having 2 to 10 carbon atoms,
and about 2 to about 90 mol % of recurring units of Formula (7):

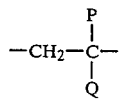
(7)

wherein P and Q each independently is a hydrogen atom, a halogen atom, a cyano group, an aryl group, a halogenophenyl group, a phenyl group substituted with one or more substituents selected from $C_1$–$C_5$ straight chain or branched alkyl and haloalkyl groups, —$COOR_9$ in which $R_9$ is a hydrogen atom or $R_{10}$, $R_{10}$ is a $C_1$–$C_{10}$ hydrocarbon residue, —$COR_9$, —$OCOR_{10}$, —$CONHR_9$, an imidazolyl group, a pyridyl group and a carbazolyl group, based on the total moles of recurring units of Formula (4) and Formula (7), and having a number-average molecular weight of about 1,000 to about 2,000,000.

9. A linear copolymer as claimed in claim 8, wherein $R_1$ is a hydrogen atom, a methyl group or an ethyl group.

10. A linear copolymer as claimed in claim 8, wherein $R_2$ and $R_3$ each independently is a hydrogen atom, a methyl group, an ethyl group, a benzyl group or a carboxymethyl group.

11. A linear copolymer as claimed in claim 8, wherein at least one of P and Q is a hydrogen atom.

12. A cross-linked copolymer comprising about 98 to about 10 mol % of recurring units of Formula (4):

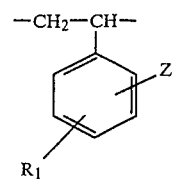
(4)

wherein $R_1$ is a hydrogen atom or a straight chain or branched hydrocarbon group having 1 to 4 carbon atoms, and Z is a group of Formula (2) or Formula (3):

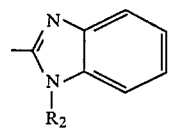
(2)
(3)

wherein $R_2$ and $R_3$ each independently is a hydrogen atom, a straight chain or branched hydrocarbon group having 1 to 10 carbon atoms or a carboxyalkyl group having 2 to 10 carbon atoms, about 2 to about 50 mol % of recurring units of Formula (5) plus Formula (6):

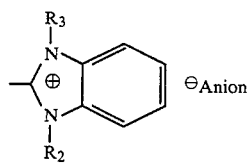
(5) (6)

wherein L, M and E each independently is a hydrogen atom or a methyl group; A is

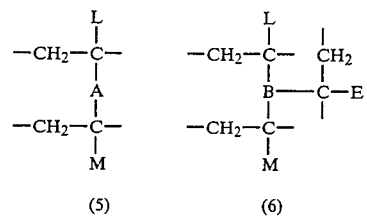

wherein $R_4$ is a hydrogen atom or a $C_1$–$C_5$ hydrocarbon residue;

wherein D is —O—, —S—, —NH— or a divalent $C_1$–$C_5$ hydrocarbon residue;

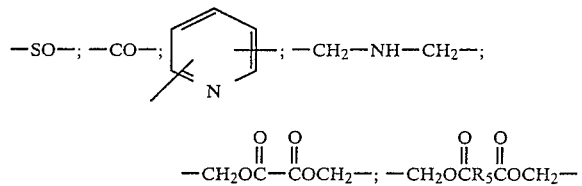

wherein $R_5$ is a divalent $C_1$-$C_8$ hydrocarbon residue;

wherein $R_6$ is a divalent $C_1$-$C_5$ hydrocarbon residue; or

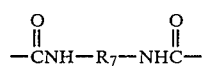

wherein $R_7$ is a divalent $C_1$-$C_3$ hydrocarbon residue; and B is

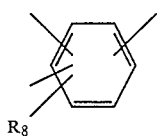

wherein $R_8$ is a hydrogen atom or a $C_1$-$C_5$ hydrocarbon residue;

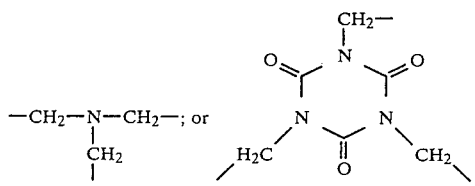

and 0 to about 88 mol % of recurring units of Formula (7):

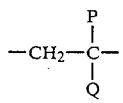

wherein P and Q each independently is a hydrogen atom, a halogen atom, a cyano group, an aryl group, a halogenophenyl group, a phenyl group substituted with one or more substituents selected from $C_1$-$C_5$ straight chain or branched alkyl and haloalkyl groups, —COOR$_9$ in which R$_9$ is a hydrogen atom or R$_{10}$, R$_{10}$ is a $C_1$-$C_{10}$ hydrocarbon residue, —COR$_9$, —OCOR$_{10}$, —CONHR$_9$, an imidazolyl group, a pyridyl group and a carbazolyl group,
based on the total moles of recurring units of Formula (4), Formula (5), Formula (6) and Formula (7).

13. A cross-linked copolymer as claimed in claim 12, wherein $R_1$ is a hydrogen atom, a methyl group or an ethyl group.

14. A cross-linked copolymer as claimed in claim 12, wherein $R_2$ and $R_3$ each independently is a hydrogen atom, a methyl group, an ethyl group, a benzyl group or a carboxymethyl group.

15. A cross-linked copolymer as claimed in claim 12, wherein at least one of L, M and E is a hydrogen atom.

16. A cross-linked copolymer as claimed in claim 12, wherein A is

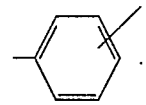

17. A cross-linked copolymer as claimed in claim 12, wherein B is

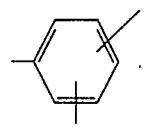

18. A cross-linked copolymer as claimed in claim 12, wherein at least one of P and Q is a hydrogen atom.

19. A process for the preparation of a basic polymer according to claim 4, which comprises polymerizing about 10 to 100 mol % of a basic compound of Formula (1):

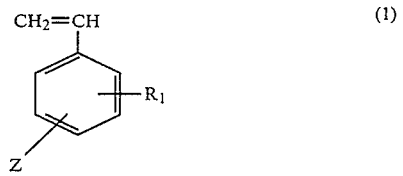

0 to about 50 mol % of at least one monomer of Formula (10) plus Formula (11):

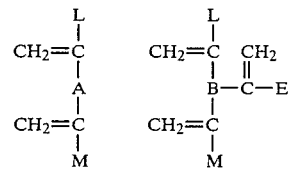

and 0 to about 88 mol % of a monomer of Formula (12):

based on the total moles of monomers of Formula (1), Formula (10), Formula (11) and Formula (12).

20. A process for the preparation of a basic polymer according to claim 4, wherein Z is a group of Formula (2);

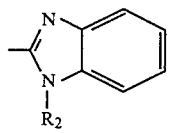
(2)

which comprises reacting a polymer comprising about 10 to 100 mol % of the recurring units of Formula (13):

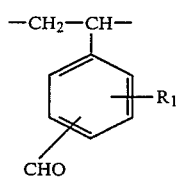
(13)

0 to about 50 mol % of recurring units of Formula (5) plus Formula (6):

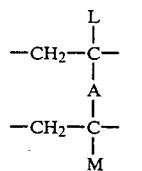 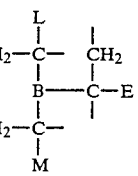

(5)  (6)

and 0 to about 88 mol % of recurring units of Formula (7);

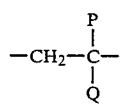
(7)

with an o-phenylenediamine of Formula (9):

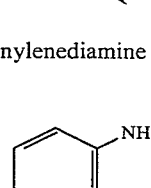
(9)

21. A process for the preparation of a basic polymer according to claim 4, wherein Z is a group of Formula (3):

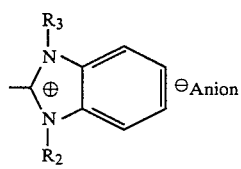
(3)

which comprises reacting a polymer comprising about 10 to 100 mol % of recurring units of Formula (4):

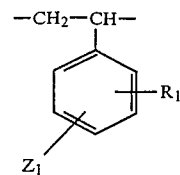
(4)

wherein $Z_1$ is a group of Formula (2):

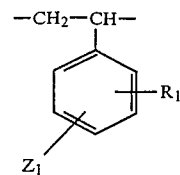
(2)

0 to about 50 mol % of recurring units of Formula (5) plus Formula (6):

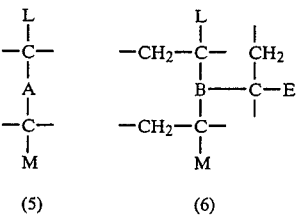

(5)  (6)

and 0 to about 88 mol % of recurring units of Formula (7):

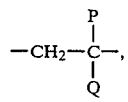
(7)

with a compound $R_3Y$ wherein Y is a halogen atom.

22. A process for the preparation of a linear homopolymer according to claim 5, which comprises polymerizating a basic compound of Formula (1):

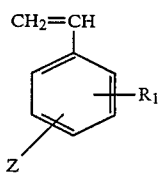
(1)

23. A process for the preparation of a linear copolymer according to claim 8, which comprises a copolymerizing about 98 to about 10 mol % of a basic compound of Formula (1):

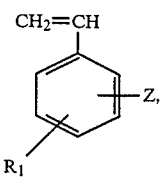
(1)

and about 2 to about 90 mol % of a monomer of Formula (12):

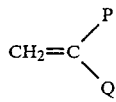
(12)

based on the total moles of monomer of Formula (1) and Formula (12).

24. A process for the preparation of a cross-linked copolymer according to claim 12, which comprises copolymerizing about 98 to about 10 mol % of a basic compound of Formula (1):

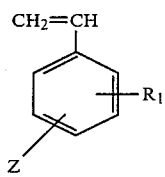
(1)

about 2 to about 50 mol % of at least one monomer of Formula (10) plus Formula (11):

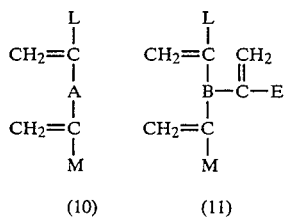
(10)　　(11)

and 0 to about 88 mol % of a monomer of Formula (12):

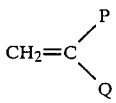
(12)

based on the total moles of monomer of Formula (1), Formula (10), Formula (11) and Formula (12).

25. A process for the preparation of a linear homopolymer according to claim 5, wherein Z is a group of Formula (2):

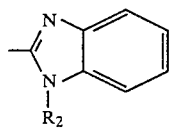
(2)

which comprises reacting a polymer comprising recurring units of Formula (13):

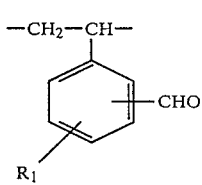
(13)

and having a number-average molecular weight of about 1,000 to about 2,000,000 with an o-phenylenediamine of Formula (9):

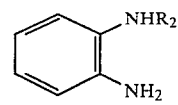
(9)

26. A process for the preparation of a linear copolymer according to claim 8, wherein Z is a group of Formula (2):

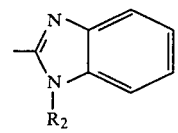
(2)

which comprises reacting a linear copolymer comprising about 98 to about 10 mol % of recurring units of Formula (13):

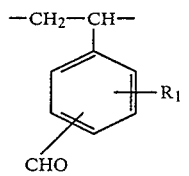
(13)

and about 2 to about 90 mol % of recurring units of Formula (7):

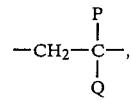
(7)

based on the total moles of recurring units of Formula (7) and Formula (13), and having a number-average molecular weight of about 1,000 to about 2,000,000, with an o-phenylenediamine of Formula (9):

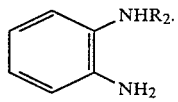
(9)

27. A process for the preparation of a cross-linked copolymer according to claim 12, wherein Z is a group of Formula (2):

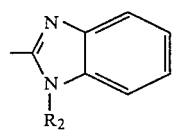
(2)

which comprises reacting a cross-linked copolymer comprising about 98 to about 10 mol % of recurring units of Formula (13):

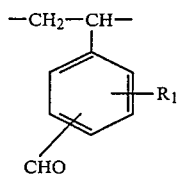 (13)

about 2 to about 50 mol % of recurring units of Formula (5) plus Formula (6):

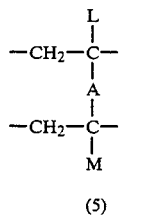 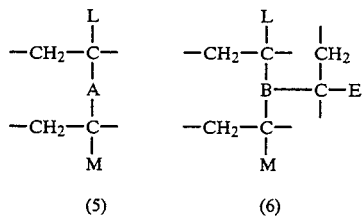

(5)   (6)

and 0 to about 88 mol % of recurring units of Formula (7):

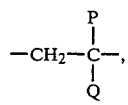 (7)

based on the total moles of recurring units of Formula (13), Formula (5), Formula (6) and Formula (7), with an O-phenylenediamine of Formula (9):

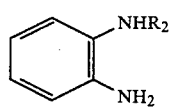 (9)

28. A process for the preparation of a linear homopolymer according to claim 5, wherein Z is a group of Formula (3):

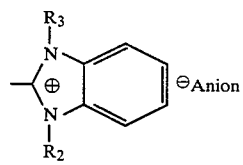 (3)

which comprises reacting a polymer comprising recurring units of Formula (4):

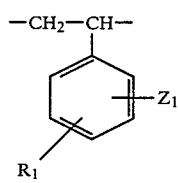 (4)

wherein $Z_1$ is a group of Formula (2):

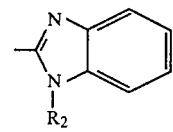 (2)

and having a number-average molecular weight of about 1,000 to about 2,000,000, with a compound $R_3Y$ wherein Y is a halogen atom.

29. A process for the preparation of a linear copolymer according to claim 8, wherein Z is a group of Formula (3):

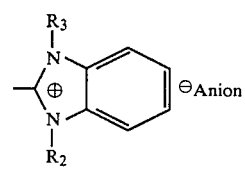 (3)

which comprises reacting a linear copolymer comprising about 98 to about 10 mol % of recurring units of Formula (4):

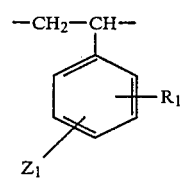 (4)

wherein $Z_1$ is a group of Formula (2):

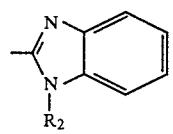 (2)

based on the total moles of recurring units of Formula (4) and Formula (7), and having a number-average molecular weight of about 1,000 to about 2,000,000, with a compound $R_3Y$ wherein Y is a halogen atom.

30. A process for the preparation of a cross-linked copolymer according to claim 12, wherein Z is a group of Formula (3):

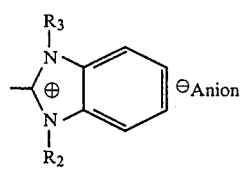 (3)

which comprises reacting a cross-linked copolymer cmprising about 98 to about 10 mol % of recurring units of Formula (4):

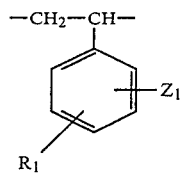

wherein $Z_1$ is a group of Formula (2):

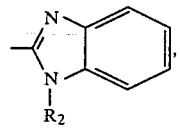

about 2 to about 50 mol % of recurring units of Formula (5) plus Formula (6):

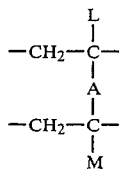 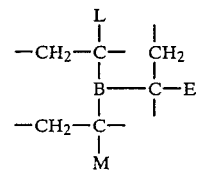

and 0 to about 88 mol % of recurring units of Formula (7):

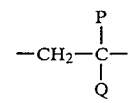

based on the total moles of recurring units of Formula (4), Formula (5), Formula (6) and Formula (7), with a compound $R_3Y$ wherein Y is a halogen atom.

31. A process as claimed in claim 24, wherein the reaction is carried out in the presence of an inert solvent.

32. A process as claimed in claim 27, wherein the reaction is carried out in the presence of an inert solvent.

33. A process as claimed in claim 30, wherein the reaction is carried out in the presence of an inert solvent.

34. A process as claimed in claim 27, wherein the reaction is carried out in the presence of a reaction promotor.

35. A process as claimed in claim 30, wherein the reaction is carried out in the presence of a basic compound.

36. In an ion exchange process employing an ion exchange resin, the improvement which comprises employing as the ion exchange resin a cross-linked copolymer comprising about 98 to about 10 mol % of the recurring units of Formula (4):

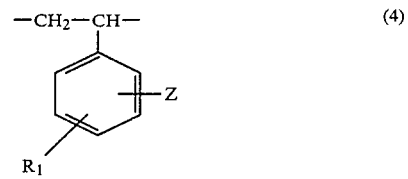

37. A process according to claim 36, wherein a cross-linked copolymer is a copolymer according to claim 12.

* * * * *